United States Patent
Han et al.

(10) Patent No.: US 12,127,872 B2
(45) Date of Patent: Oct. 29, 2024

(54) VOLUMETRIC IMAGE GUIDANCE FOR IMPROVED PATHOLOGY SECTIONING AND ANALYSIS OF TISSUE SAMPLES

(71) Applicant: CLARIX IMAGING CORPORATION, Chicago, IL (US)

(72) Inventors: Xiao Han, Chicago, IL (US); Christian Wietholt, Naperville, IL (US)

(73) Assignee: Clarix Imaging Corporation, Chicago, IL (US)

( * ) Notice: Subject to any disclaimer, the term of this patent is extended or adjusted under 35 U.S.C. 154(b) by 242 days.

(21) Appl. No.: 17/798,848

(22) PCT Filed: Feb. 26, 2021

(86) PCT No.: PCT/US2021/020020
§ 371 (c)(1),
(2) Date: Aug. 10, 2022

(87) PCT Pub. No.: WO2021/174078
PCT Pub. Date: Sep. 2, 2021

(65) Prior Publication Data
US 2023/0086976 A1 Mar. 23, 2023

Related U.S. Application Data

(60) Provisional application No. 62/983,065, filed on Feb. 28, 2020.

(51) Int. Cl.
*A61B 6/00* (2024.01)
*A61B 6/03* (2006.01)
(Continued)

(52) U.S. Cl.
CPC ............ *A61B 6/462* (2013.01); *A61B 6/032* (2013.01); *A61B 6/469* (2013.01); *A61B 6/5223* (2013.01);
(Continued)

(58) Field of Classification Search
CPC ............ G06T 7/11; G06T 2207/10116; G06T 2207/20061; G06T 2207/30204;
(Continued)

(56) References Cited

U.S. PATENT DOCUMENTS 9,895,121 B2 * 2/2018 Abdolell ................ A61B 6/502
2008/0087833 A1 4/2008 McCroskey et al.
(Continued)

OTHER PUBLICATIONS

Nicolau et al., "Augmented reality in laparoscopic surgical oncology", Surgical Oncology, 20 (2011) 189-201.
(Continued)

*Primary Examiner* — Don K Wong
(74) *Attorney, Agent, or Firm* — McDonnell Boehnen Hulbert & Berghoff LLP

(57) ABSTRACT

Embodiments are provided for improved analysis of surgically explanted pathology samples or other varieties of tissue sample by guiding the sectioning of those samples using high-resolution volumetric imaging data. Such imaging data can include micro-CT imaging data. Improved sample imaging and visualization methods facilitate pathological analysis of the sample, guiding the sectioning of the sample to planes most likely to provide highly valuable and accurate data about sample margins relative to tumors or other target structures, tissue type cell morphology or other properties of a tumor or other target structure, or other clinically relevant data that could be missed were the tissue sample not sectioned along such image-guided plane(s). A projector or augmented-reality device can be used to indicate, to a pathologist, the location of structures of interest within the sample and/or the location of a sectioning gig could be detected/controlled relative to a display of the imaging data.

35 Claims, 13 Drawing Sheets

(51) Int. Cl.
*A61B 6/46* (2024.01)
*G06T 7/11* (2017.01)

(52) U.S. Cl.
CPC ...... *G06T 7/11* (2017.01); *G06T 2207/10081* (2013.01); *G06T 2207/30024* (2013.01)

(58) Field of Classification Search
CPC ... A61B 6/5211; A61B 6/5217; A61B 6/5223; A61B 6/545; A61B 6/547; A61B 6/46; A61B 6/461; A61B 6/467; A61B 6/469; A61B 6/462; A61B 6/463; A61B 6/464; A61B 6/465
See application file for complete search history.

(56) References Cited

U.S. PATENT DOCUMENTS

| | | |
|---|---|---|
| 2014/0086463 A1 | 3/2014 | Meetz et al. |
| 2015/0306423 A1 | 10/2015 | Bharat et al. |
| 2017/0086665 A1 | 3/2017 | Klein et al. |
| 2019/0021681 A1 | 1/2019 | Kohli et al. |
| 2019/0321065 A1 | 10/2019 | Yilmaz et al. |

OTHER PUBLICATIONS

The International Search Report (ISR) with Written Opinion for PCT/US2021/020020 dated May 10, 2021, pp. 1-11.

* cited by examiner

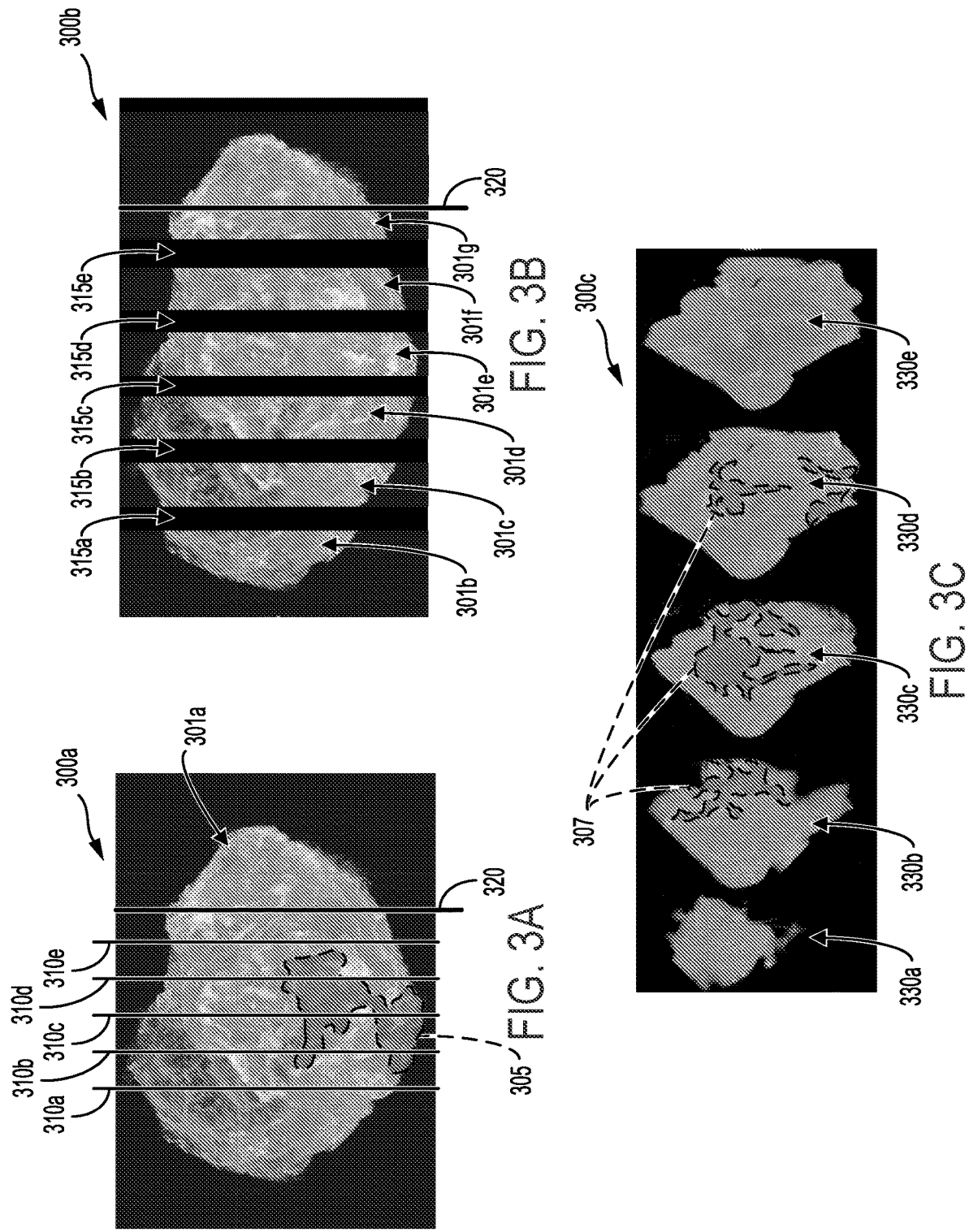

VOLUMETRIC IMAGE GUIDANCE FOR IMPROVED PATHOLOGY SECTIONING AND ANALYSIS OF TISSUE SAMPLES

CROSS-REFERENCE TO RELATED APPLICATIONS

This application calls priority to U.S. provisional application No. 62/983,065, filed Feb. 28, 2020 and PCT application PCT/US21/20020, filed Feb. 26, 2021, the contents of which are hereby incorporated by reference. The contents of U.S. Pat. No. 8,605,975, filed Oct. 11, 2010, U.S. application no. 2014/0161332, filed Dec. 2, 2013, U.S. Pat. No. 9,189,871, filed Dec. 29, 2014, U.S. Pat. No. 9,613,442, filed Nov. 5, 2015, PCT application no. US18/52175, filed Sep. 21, 2018, U.S. Provisional Patent Application No. 62/562,138, filed on Sep. 22, 2017, and International Application PCT/US20/62462, filed Nov. 26, 2020, are also hereby incorporated by reference.

BACKGROUND

The treatment for a variety of health conditions can include the removal of specified tissues from the body. For example, treatment of certain cancers can include surgically removing one or more tumor masses from the body. Other conditions can be treated by removal of other types of tissue, foreign bodies, or other masses from the body. In performing such a removal, it is desirable to ensure complete removal of the target tissue while removing as little as possible of nearby healthy tissue. In practice, surgeons will often remove additional tissue around the target in order to ensure that the target is fully removed (e.g., to prevent relapse due to remnant tumor tissue continuing to grow).

To improve patient health outcomes, a pathologist can analyze the explanted tissue in order to determine whether the entire target has been removed, to determine a type of tissue that was explanted (e.g., to verify that an explanted target structure was a malignant tumor), to perform DNA sequencing or other analysis on the explanted tissue (e.g., to tailor systemic anti-cancer treatments), or to provide some other benefit to the patient and/or to the general treatment of illness. This can include sectioning the sample in order to visually, microscopically, or otherwise optically inspect a target within the tissue sample. This inspection may permit the pathologist to identify the type of tissue in the target (e.g., malignant cancerous tissue, benign tumor tissue), a status of the target (e.g., likely to be pre or post metastatic), and whether the target was fully removed as a result of explanation of the tissue sample (e.g., by observing how close to a margin of the tissue sample the target tissue extends). The pathologist can then provide a final diagnosis as to the success of the target removal procedure, which may then be used to decide whether to perform an additional procedure to remove portions of the target that may remain in the patient.

SUMMARY

An aspect of the present disclosure relates to a method including: (i) receiving volumetric density information about a target sample; (ii) determining, based on the volumetric density information, a location of at least one region of interest within the target sample; and (iii) providing an indication of the location of the at least one region of interest within the target sample, wherein providing the indication comprises at least one of: (1) projecting, onto the target sample, a visual pattern that is indicative of the location of the at least one region of interest within the target sample, or (2) providing, via a display of a head-mounted display, a visual pattern such that the location of the at least one region of interest within the target sample is, from a perspective of a wearer of the head-mounted display, indicated across a surface of the target sample.

Another aspect of the present disclosure relates to a method including: (i) receiving volumetric density information about a target sample; (ii) detecting a location and/or an angle of a sectioning tool relative to the target sample; and (iii) providing, on a display, a visual indication of the volumetric density information and an indication of the detected location and/or angle of the sectioning tool relative to the volumetric density information.

Another aspect of the present disclosure relates to a method including: (i) receiving volumetric density information about a target sample; (ii) receiving a location and/or an angle, relative to the volumetric density information, of a target section through the target sample; and (iii) causing an actuator to align a sectioning tool with the target sample according to the received location and/or angle of the target section.

Yet another aspect of the present disclosure relates to a transitory or non-transitory computer-readable medium configured to store at least computer-readable instructions that, when executed by one or more processors of a computing device, causes the computing device to perform controller operations to perform the method of any of the above aspects.

Yet another aspect of the present disclosure relates to a system including: (i) a controller comprising one or more processors; and (ii) a transitory or non-transitory computer-readable medium having stored therein computer-readable instructions that, when executed by the one or more processors of the controller, cause the system to perform the method of any of the above aspects.

These as well as other aspects, advantages, and alternatives will become apparent to those of ordinary skill in the art by reading the following detailed description with reference where appropriate to the accompanying drawings. Further, it should be understood that the description provided in this summary section and elsewhere in this document is intended to illustrate the claimed subject matter by way of example and not by way of limitation.

BRIEF DESCRIPTION OF THE FIGURES

FIG. 3A depicts an example display of data related to a target sample.
FIG. 3B depicts an example display of data related to a target sample.
FIG. 3C depicts an example display of data related to a target sample.

DETAILED DESCRIPTION

Figure 1B:
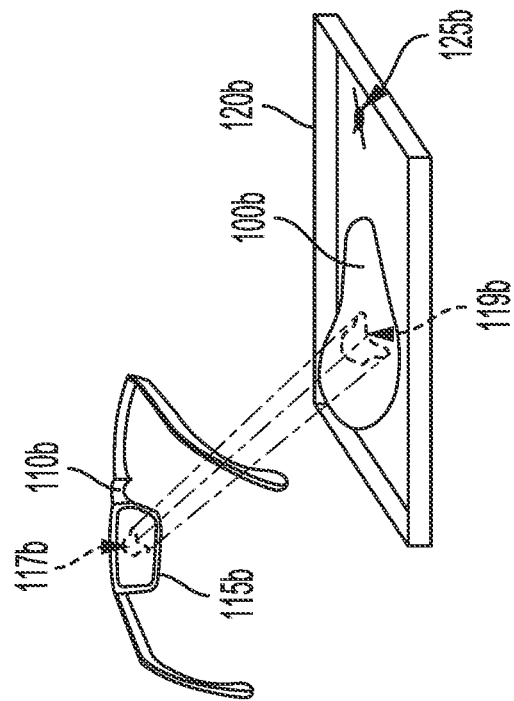
FIG. 1B depicts elements of an example system.

Examples of methods and systems are described herein. It should be understood that the words "exemplary," "example," and "illustrative," are used herein to mean "serving as an example, instance, or illustration." Any embodiment or feature described herein as "exemplary," "example," or "illustrative," is not necessarily to be construed as preferred or advantageous over other embodiments or features. Further, the exemplary embodiments described herein are not meant to be limiting. It will be readily understood that certain aspects of the disclosed systems and methods can be arranged and combined in a wide variety of different configurations.

I. OVERVIEW

A variety of clinical interventions involve the removal of tumors or other undesirable tissue or substances. Ideally, only the unwanted tissue would be removed, sparing neighboring tissue. This is difficult to achieve in practice, so surgeons will often excise more tissue than is necessary so as to prevent leaving any of the unwanted tissue in the body where it can, e.g., lead to relapse. However, this must be balanced in order to spare healthy tissue, so as to improve-post operative outcomes with respect to tissue function and appearance. Thus, explanted tissue is often analyzed by a pathologist in order to determine whether the procedure was successful in fully removing a tumor or other target tissue/structure. The pathologist's diagnosis can then be used to determine whether to perform an additional procedure (to remove additional tissue), where to remove such tissue (e.g., at a location in the patient's body corresponding to a location of the tissue sample at which a tumor approaches and/or clearly exceeds the boundary of the tissue sample), whether to provide chemotherapy or other systemic treatments, or other healthcare decisions. The pathologist may also use optical inspection (e.g., microscopy), tissue staining, DNA sequencing, antibody tests, or other procedures to identify properties of the target tissue (e.g., to determine whether the target was benign or cancerous, to determine a cancer sub-type to inform the selection of systemic treatments).

Pathological analysis of such tissue samples generally includes sectioning the sample one or more times to permit the composition of the tissue sample throughout its volume to be observed in order to determine the type and extent of tumors or other contents of the tissue sample. This can include creating a set of slices of the sample (via repeated sectioning) and then staining or otherwise manipulating the slices to permit microscopic optical imaging of the slices or other analyses. It is generally desirable to obtain slices through tumors or other contents of interest, and in particular to obtain slices that depict how close the tumor or other target contents are to the margin (or outer surface) of the tissue sample. This may be done so as to determine whether the tumor or other target contents were likely to have been completely removed as part of removal or the tissue sample. If not, further procedure(s) to remove additional amount of tissue may be planned in order to ensure that the tumor or other target contents have been completely removed from a patient's body.

A tissue sample may be sectioned in such a manner as to produce so many slices, at such a high spatial resolution, as to permit the entire volume of the sample to be analyzed. In practice, however, the pathologist's time and laboratory resources are limited, so a more limited number of sections/slices are usually performed and analyzed. The location and/or angle of such sections are usually determined by the pathologist on the basis of visual inspection of the outer surface of the tissue sample and based on palpation of the sample to determine where a tumor or other target is location within the sample. The sample can then be sectioned so as to generate slices through the target, e.g., through the perceived center of a tumor, or through a cross-section of the tumor that is likely to closely approach a margin of the sample.

However, this subjective approach may result in sections through the sample that do not accurately represent how closely a tumor or other target structure approaches the sample margin. Alternatively, there may be instances where a tumor or other target within the sample is difficult or impossible to detect via palpation, but that may be visible using X-rays or other imaging modalities. For example, many tumors (e.g., breast cancer tumors) may exhibit a characteristic pattern of calcification that is evident in X-ray images of the tumor but is imperceptible via palpation, due to having similar mechanical properties to non-calcified breast tissue. Thus, a pathologist operating in such a manner may generate a false negative diagnosis with respect to whether a tumor has been fully removed. In the case of determining whether a breast cancer tumor has been fully removed based on analysis of the explanted breast tissue sample, this false negative rate can be as high as 40%. Such false negatives can have significant negative impacts on patient health, including disease progression and/or death resulting from failure to detect the remnant tumor tissue and/or delay in removing the remnant tumor tissue.

Embodiments described herein provide a variety of benefits, including benefits that address the above issues. These embodiments include indicating volumetric density information for tissue samples (e.g., micro-CT or MRI imaging data of tissue samples) in a manner that is relative to the tissue samples, so as to guide a pathologist's sectioning and analysis of the tissue sample. Additionally or alternatively, a jig or other sectioning tool may be registered to such imaging data. This can allow the number of sections/slices taken from the sample to be reduced (thereby reducing cost and/or pathologist time). Additionally or alternatively, the value of each section/slice made may be increased by using the volumetric density information to target tumors or other targets within the sample, ensuring that the target is correctly localized and sectioned and also ensuring that the representation of the target in a particular section is maximally valuable (e.g., sectioning a tumor through the cross-section across which it has the greatest area/dimension, or along which it comes closest to the sample margin). These methods allow both the location and angle of the sections to be determined, allowing for sections that are improved relative to conventional sections which are often restricted to orthogonal planes/angles. Yet further, the embodiments described herein also allow for the detection, localization, and sectioning of tumors or other targets that would be imperceptible or otherwise difficult to detect (e.g., calcified breast tumor tissue that is indistinguishable from normal tissue via palpation).

These embodiments can include projecting an indication of the extent of a tumor, the location/angle of a target section, or some other region of interest onto a tissue sample so as to guide a pathologist, pathologist's assistant, or other healthcare professional in sectioning the tissue sample. Additionally or alternatively, a head-mounted display or other augmented reality apparatus could be used to provide a user with the perception of such information having been projected onto the tissue sample. In some examples, the location and/or angle of a jig or other sectioning tool could be detected and indicated on a display relative to a display of the volumetric density information or some other indication of the target sample (e.g., a target reticule) to facilitate aligning the sectioning tool with a region of interest within the sample and/or with a target section through the sample. Additionally or alternatively, the location and/or angle of such a sectioning tool could be automatically controlled (e.g., by a pathologist working at a remote pathologist's workstation). Such implementations could allow a single pathologist to manage the sectioning of an increased number of samples by relying on assistants and/or automated systems to perform the sectioning of the samples based on the pathologist's selection of the location and/or angle of target section(s) through each of the samples.

Also provided are improvements in the visualization of a tumor or other regions of interest within a tissue sample. These improvements include color-coding the surface of a target volume within the sample according to how close the nearest margin of the sample is to the segment. This can provide a clear indication to the pathologist as to where the target (e.g., tumor) might have extended past the edge of the sample, indicating that there may be more of the target still in the patient's body and where that remnant target is located. Such color-coding may be provided on a display and/or via projection onto the target sample.

It should be understood that the above embodiments, and other embodiments described herein, are provided for explanatory purposes, and are not intended to be limiting.

II. EXAMPLE SYSTEMS FOR IMAGE-GUIDED PATHOLOGY

As noted above, it can be beneficial to use micro-CT or other volumetric density information to guide the sectioning or other pathological preparation and analysis of tissue samples. Such image-guided pathology can provide many benefits, including the detection of tumors or other targets that would be undetectable by a pathologist without imaging guidance, improving the accuracy of diagnosis/analysis of a sample by sectioning the sample at more optimal locations/angles (e.g., to more accurately capture the relationship between a tumor or other target and the sample margin), reducing the cost or time associated with sample analysis by facilitating the use of fewer sections by more accurately sectioning the sample through one or more specified targets, and/or providing other benefits.

Some of these benefits can be partially provided by performing micro-CT or other volumetric imaging on a tissue sample prior to a pathologist sectioning or otherwise analyzing the sample. However, the embodiments herein provide additional benefits by corresponding the volumetric density information (e.g., one or more regions of interest determined therefrom) to the physical tissue sample. This can include providing some manner of indication to a pathologist or other healthcare professional of the relationship between a region of interest and the corresponding portion of the tissue sample. For example, a projector could project light onto the tissue sample to indicate the extent of tumor within the sample or to indicate a location/angle of a target section through the sample. In another example, the location/angle of an instrumented jig or other sectioning tool relative to the tissue sample could be detected and indicated on a display relative to an indication of the volumetric density information. Additionally or alternatively, the location and/or angle of a target section through a sample could be determined relative to the volumetric density information for the sample and used to drive a jig or other sectioning tool to the corresponding location and/or angle relative to the physical tissue sample, thereby facilitating the manual or automated sectioning of the tissue sample according to the target section.

Figure 1A:
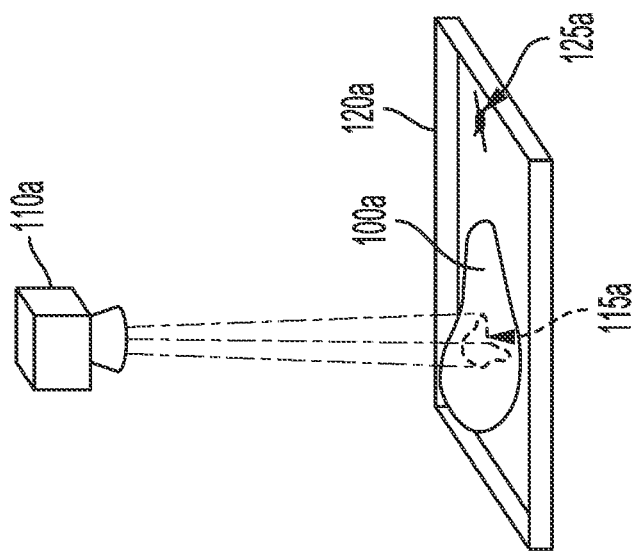
FIG. 1A depicts elements of an example system.

In some examples, this can include projecting, onto the target sample, a visual pattern that is indicative of the location of the at least one region of interest within the target sample. FIG. 1A depicts elements of such an embodiment. FIG. 1A depicts a projector 110a that is projecting a visual pattern 115a onto a tissue sample 100a that is indicative of the location and geometry of a tumor within the tissue sample 100a. The tissue sample 100a is located within a sample receptacle 120a. The sample receptacle 120a may contain a fiducial 125a or other features to allow for registration of the projector 110a with the tissue sample 100a and/or volumetric density information therefor, thereby ensuring that any patterns (e.g., 115a) projected by the projector 110a are projected accurately onto the correct portion of the tissue sample 100a.

Alternatively, a head-mounted display or other augmented reality apparatus could be employed to provide the perception of such projection to a pathologist or other user. This could be done, e.g., to providing a visual pattern such that the location of at least one region of interest within the target sample is, from a perspective of a wearer of the head-mounted display, indicated across a corresponding surface of the target sample. Thus, the visual pattern could change as the location of the head-mounted display and/or user's eye(s) changes so as to reflect the corresponding changes in the location and angle of the tissue sample relative to the display and/or user's eye(s). FIG. 1B depicts elements of such an embodiment, showing a head-mounted display 110b that includes a display 115b. A visual pattern 117b is being provided via the display 115b such that, from a perspective of a wearer of the head-mounted display 110b, the location and geometry of a tumor within the tissue sample 100b appears across a corresponding surface 119b of the target sample 100b. The tissue sample 100b is located within a sample receptacle 120b. The sample receptacle 120b may contain a fiducial 125b or other features to allow for registration of the head-mounted display 110b with the tissue sample 100b and/or volumetric density information therefor, thereby ensuring that any patterns (e.g., 117b) provided by the display 115b result in a user perceiving an accurate depiction of the tumor across the correct portion of the tissue sample 100b.

The visual pattern could be an indication of the raw volumetric density information (e.g., a projection of the density onto a plane or surface) and/or a filtered or otherwise computationally modified version thereof. For example, the visual pattern could be an indication of the extent of a tumor or other target (e.g., a staple, a wire, an accumulation of a contrast agent, a duct, a blood vessel, or a calcification, etc.) within the target sample, as identified from and/or relative to the volumetric density information for the target sample. Such a visual pattern could be color-coded or otherwise patterned to provide information about the proximity of the outer surface of the tumor or other target to the outer surface of the tissue sample, e.g., to facilitate a pathologist sectioning the tissue sample in such a manner that the completeness of removal of the tumor can be more accurately assessed. Additionally or alternatively, the visual pattern could include a line or other pattern indicating the location and/or angle of a target section through the tissue sample, thereby guiding a pathologist to effect sectioning of the tissue sample according to a target section determined relative to the volumetric density information. Such a target section could be manually selected by a pathologist with reference to the volumetric density information and/or automatically generated based on the volumetric density information.

Additionally or alternatively, an instrumented jog or other sectioning tool could be provided whose location and/or angle, relative to a tissue sample, is detectable and/or controllable. The detected location of such a sectioning tool could then be indicated on a display relative to a display of volumetric density information for the sample, relative to an indication of one or more regions of interest within the sample, relative to an indication of a 'target' location/angle (which may be generated automatically and/or specified by a pathologist, as described below), or relative to some other information related to the volumetric density information for the sample. Once the sectioning tool's detected location is aligned with a target section, it can be locked or otherwise used to section the sample according to the target section. This could include passing a saw, knife, vibrating blade or other sectioning means through a guide channel of the sectioning tool. Alternatively, the sectioning tool could, itself, include some automated sectioning means which could be operated to section the sample. Additionally or alternatively, the sectioning tool could include actuators (e.g., servos, hydraulic or pneumatic cylinder, ball screws) to control the location and/or angle of the sectioning tool relative to the tissue sample to correspond to a target section through the sample. In such examples, a pathologist could remotely operate such a system to section the tissue sample without being physically present.

Figure 2:
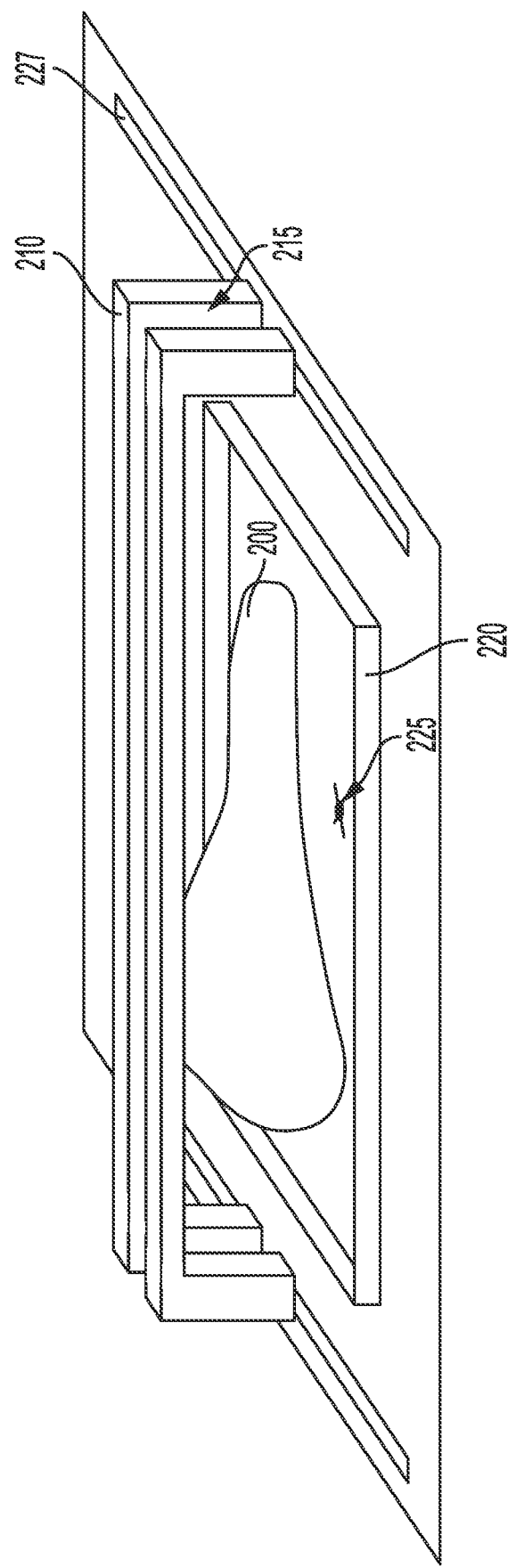
FIG. 2 depicts elements of an example system.

FIG. 2 depicts an example of such a system. FIG. 2 depicts a sectioning tool 210 that is movable, along rails 227, relative to a tissue sample 200. The angle of the sectioning tool 210 relative to the tissue sample 200 may also be detectable and/or controllable. The tissue sample 200 is located within a sample receptacle 220. The sample receptacle 220 may contain a fiducial 225 or other features to allow for registration of the sectioning tool 210 with the tissue sample 200 and/or volumetric density information therefor, thereby ensuring that the location and/or angle of the sectioning tool 210 relative to the sample 200 is accurately detected and/or controlled. The sectioning tool 210 includes a guide 215 through which a saw, knife, vibrating blade, or other sectioning means may be passed to section the sample 200 though a section that may be displayed on a screen (e.g., overlaid onto a visualization of volumetric density information, regions of interest, or some other information about the tissue sample 200) and/or that may be automatically controlled to correspond to a specified target section. Additionally or alternatively, an automated blade or other sectioning means could be incorporated into the sectioning tool 210.

As briefly noted above, the projection of visual patterns onto a tissue sample and/or the detected and/or control of the location and/or angle of a sectioning tool relative to a tissue sample may be performed in connection with one or more displays that are indicative of volumetric density information for the tissue sample and/or other information related thereto. Such display(s) could be part of a user interface that allows a user to interact with the volumetric density information to change how the information is displayed, to identify regions of interest (e.g., tumors) within the volumetric density information, to specify the location, extent, and geometry of such regions of interest (e.g., to input the properties of a segmentation map that represents the extent of a tumor and/or to input modifications to such a segmentation map that has been generated by an algorithm based on the volumetric density information), to change the orientation of the display of the volumetric density information, or to otherwise interact with the volumetric density information and/or to control the display thereof.

This could include specifying the location and/or angle of one or more target sections relative to the volumetric density information. This could include manually specifying the location and/or angle, relative to a display of the volumetric density information, of a target section through the tissue sample. Additionally or alternatively, such a location and/or angle of a target section could be determined automatically based on the volumetric density information. For example, an algorithm could be used to generate a target section through the tissue sample such that the area or greatest dimension of a cross-section through a region of interest (e.g., through a segmentation map representing the extent of the region of interest) is maximized or increased relative to one or more alternative sections through the tissue sample. This could be done to ensure that the region of interest (e.g., tumor), when imaged along that target section, is accurately represented with respect to size, shape, texture, or other properties. Additionally or alternatively, an algorithm could be used to generate a target section through the tissue sample such that the target section passes through a region of "closest approach" between the region of interest and an outer surface or margin of the tissue sample. This could be done to ensure that images of the tissue sample taken along that target section can be used to accurately assess the likelihood that a target represented by the region of interest (e.g., tumor) extended beyond the margin of the tissue sample.

Such specified target sections could be projected onto a tissue sample (e.g., as an indicate region of interest projected by the projector 110a or displayed via the display 115b) to guide sectioning of the tissue sample. In another example, an actuated sectioning tool could be operated to align with a tissue sample according to such specified target sections. In yet another example, the detected location and/or angle of an instrumented sectioning tool could be indicated on a display relative to such specified target sections. This could include indicating both the location and/or angle of the target section and the detected location and/or angle of the sectioning tool (e.g., overlaid on a visual display of the volumetric density information), or providing some other indication to guide a user to align the sectioning tool with the tissue sample according to the target section (e.g., by providing a target on a screen and a reticle whose location relative to the target represents the difference between the target and detection location and/or angle).

FIG. 3A depicts an example user interface 300a that includes an indication of volumetric density information 301a for a tissue sample along with an indication of a region of interest 305 (e.g., a tumor) overlaid thereon. Also indicated are the locations of a number of target sections 310a-e. These target sections could be manually specified by a user (e.g., by clicking or pressing on a location on the user interface, by dragging a pre-existing indicated target section) and/or determined algorithmically based on the volumetric density information. Also indicated is the detected location of a sectioning jig 320 relative to the indication of the volumetric density information 301a. The user interface 300a could also include elements or features for changing the location and/or angle of the target sections 310a-e, for changing a type of display or processing applied to the volumetric density information, for determining and/or modifying the region of interest 305, for changing and angle and/or location from which the volumetric density information is displayed, or other functions.

To assist a pathologist in specifying or selected the target sections along which to section a tissue sample, a user interface could be provided that simulated the effect of such sectioning on the tissue sample. For example, the tissue sample could be represented as having been cut into a number of separated sections. FIG. 3B depicts an example user interface 300b that includes an indication of separated segments 301b-g of volumetric density information for the tissue sample depicted in FIG. 3A along with an indication of the detected location of the sectioning jig 320 relative to the indications of the segments 301b-g of the volumetric density information. The regions 315a-e between the segments 301b-g correspond to the target sections 310a-e depicted in FIG. 3A.

In another example, a depiction of the resulting two-dimensional slices along the target sections could be provided. FIG. 3C depicts an example user interface 300c that includes two-dimensional visual depictions 330a-e of the volumetric density information along respective target section 310a-e through the target sample. Also provided is an indication of cross-sectional areas 307 which represent the intersection of the region of interest 305 (e.g., of a segmentation map that represents the extent of the region of interest relative to the volumetric density information) with the target sections 310b-d that intersect with the region of interest 305. Each of the two-dimensional visual depictions 330a-e could be colorized to simulate the appearance of the tissue sample if it was sectioned along the corresponding target section. This could include determining a cross-sectional color coding for each target section that color-codes a plurality of points across each target section based on the density of respective proximate portions of the volumetric density information. Additional information about determining such a color coding based on the volumetric density information is provided in relation to FIG. 6A below.

A user interface could provide more than one of the displays depicted in FIGS. 3A-C, or some other display depicted herein, at the same time.

The tissue sample could be prepared to facilitate sectioning of the sample while reducing deformation of the sample. For example, the tissue sample could be frozen prior to imaging and/or sectioning. In some examples, the tissue sample could be chemically fixed (e.g., using formalin or some other protein cross-linking agent) to stiffen the sample prior to imaging and/or sectioning. Additionally or alternatively, the tissue sample could be embedded within a material (e.g., agar, a 3D-printed support jig) to support the sample prior to imaging and/or sectioning.

In some examples, a pathologist in control of the sectioning tool 210 or other apparatus described herein (e.g., the sample 110a, 110b, 210 in its sample receptacle 120a, 120b, 220, which may be disposed on a pathology work table or on or within some other apparatus) may be present in the same room or as the tissue samples so as to personally perform or supervise the sectioning of tissue samples. However, the embodiments described herein allow a single pathologist to identify, select, or otherwise specify one or more target sections through tissue samples that are remote from the pathologist, based on volumetric density information for those samples. For example, a pathologist's remote workstation could be located in a pathologist's office, a pathologist's home, or some other remote location where a pathologist, radiologist, or other healthcare professional would want to access and interact with imaging data of a tissue sample. The remote workstation could provide a user interface (e.g., user interfaces like those illustrated in FIGS. 3A-C) for accessing and interacting with imagery determined from and related to volumetric density information of a target sample and for specifying target sections through the sample. The pathologist-specified target sections can then be transmitted to a pathology lab or other facility/facilities where subordinate pathologists, pathology assistants, automated apparatus (e.g., the sectioning tool 210), or other individuals or systems can section the samples according to the specified target sections. This can reduce costs by allowing the single pathologist's experience in analyzing samples to be applied to a greater number of samples per unit time, while the actual sectioning, physical preparation (e.g., staining), and imaging of the sections samples is performed by technicians and/or automated systems. This can also improve flexibility in staffing by allowing the pathologist to be physically remote from the pathology lab.

The fiducials 125a, 125b, 225 depicted in FIGS. 1A, 1B, and 2 could be used to register a projector, head-mounted display, sectioning tool, and/or other components with the physical location of a tissue sample. This could facilitate the generation of visual displays are projected onto, or appear to be, on the correct location relative to the tissue sample and/or the detection or control of the alignment of a sectioning tool with the tissue sample. Such fiducials could be detected via cameras or other means (e.g., by a camera of the head-mounted display 110b in order to render a visual pattern 117b that results in a user perceiving the correct indication across the correct surface 119b of the target sample 100b). Additionally or alternatively, such a fiducial could be a radiopaque element or other feature to facilitate imaging via micro-CT, MRI, or some other volumetric means. Such a fiducial would thus be represented in the volumetric density information for a tissue sample, thereby allowing for registration of the volumetric density information with the physical location and extent of the sample receptacle. Alternatively, such a fiducial could be omitted in examples where the alignment between the sample receptacle and other components (e.g., imaging apparatus, projector, sectioning tool) is controlled by features of the sample receptacle, e.g., by the sample receptacle having a single secure location and orientation when located within an imaging apparatus and when on a pathology work surface. In examples wherein the tissue sample is imaged within the same apparatus that is used to section the sample, the fiducials and/or sample receptacle could be omitted entirely, as the location and orientation of the imaging apparatus relative to the projector, sectioning apparatus, etc. may be measured or otherwise determined and used for registration.

An imaging apparatus used to generate volumetric density information as described herein could include a variety of components to facilitate a variety of different volumetric imaging modalities. In some examples, the imager could include high-power magnets (e.g., superconducting magnets), bias coils, radiofrequency scan coils, and other elements configured to perform magnetic resonance imaging (MRI) of the sample. Such an MRI imager could generate volumetric density information for the target sample related to the density of hydrogen atoms, MRI contrast medium atoms (e.g., Gadolinium), or related to the density of some other magnetic particle. In some examples, the imager could include a micro-CT imager configured to generate volumetric density information for the target sample related to the X-ray radiodensity or radiopacity of the sample.

Such a micro-CT imager includes at least one X-ray source, capable of generating X-rays, and at least one X-ray imager, capable of generating images of the emitted X-rays after having passed through the target sample. Higher-density regions of the target sample (which may alternatively be referred to as regions having higher X-ray radiodensity or radiopacity) will absorb and/or scatter the emitted X-rays to a greater degree, resulting in corresponding regions of the X-ray imager being exposed to a lower intensity of X-rays. A micro-CT imager operates to generate scan data in the form of a plurality of X-ray images of a target sample, each image taken at a respective angle and/or location relative to the target sample. The plurality of X-ray images of a target sample can then be reconstructed to generate volumetric density information for the target sample.

The X-ray source could include an X-ray tube, a cyclotron, a synchrotron, a radioactive X-ray source, or some other source of X-rays. The X-ray source could include multiple different sources of X-rays, e.g., to permit modulation of the beam power, beam width, the direction of the X-ray beam relative to a target sample, a focus or divergence of the X-ray beam at the location of a target sample, or to allow control of some other property of the emitted X-rays so as to facilitate imaging of a target sample.

The X-ray imager could include a photostimulable phosphor plate, scintillator, X-ray intensifier, or other element to convert X-rays into visible light coupled to a charge-coupled device, array of photodetectors, flat-panel detectors, or other visible-light imaging element(s). Additionally or alternatively, the X-ray imager could include an amorphous selenium element or some other element configured to convert X-rays directly into electron-hole pairs or other electronically-detectable phenomena. The X-ray imager and X-ray source together define a field of view, which is a region that the micro-CT imager can image. Thus, the micro-CT imager can generate an X-ray image of portions of a target sample (or other substances or structures) that are located within the field of view.

Micro-CT imaging of samples that have been removed from a body allows for the use of higher-intensity and longer-duration scans than would be possible when imaging parts of a living patient's body. Additionally, the X-ray source and X-ray imager can be located closer to the sample. These factors contribute to increased image resolution and contrast when compared to imaging tissues located within a patient's body. Further, the location and orientation of an explanted tissue sample can be arbitrarily rotated and/or translated by an actuated gantry, allowing the exact location and orientation of the sample relative to the imaging apparatus to be arbitrarily and precisely controlled. For example, X-ray images can be taken of the sample at non-uniform angles or some other reduced or sparse set of angles. Additionally, when the entire sample is small enough to fit entirely within the field of view of the imaging apparatus, the actuated gantry can be operated to ensure that the sample is, in fact, located entirely within the field of view. In some examples, a sample receptacle configured to contain the sample could have a size that is approximately coextensive with the field of view, ensuring that any sample deposited therein will remain entirely within the field of view. Alternatively, when the sample is too large to fit entirely within the field of view, the location and orientation of the sample can be controlled to obtain X-ray images at specific relative locations and orientations sufficient to allow reconstruction of volumetric density information for the entire sample.

Imaging of explanted tissue samples also allows the X-ray source to be entirely enclosed within X-ray shielding material (e.g., lead sheeting) when the X-ray source is being operated to emit X-rays. For example, a door composed of X-ray shielding material could be translated and/or rotated into place after the sample has been deposited within the micro-CT imager, reducing the amount of X-ray exposure experienced by surgeons, nurses, or other persons in proximity to the imager. This can also allow the intensity of X-rays emitted by the X-ray source to be increased while maintaining environmental exposure limits below a specified safe level, potentially increasing image resolution and/or contrast.

A micro-CT imager used to generate volumetric density information as described herein could be operated in a variety of ways to generate X-ray scan data of a sample sufficient to generate an accurate reconstruction of volumetric density information for the sample. The reconstruction methods described in U.S. Pat. No. 8,605,975, U.S. application no. 2014/0161332, U.S. Pat. No. 9,189,871, U.S. Pat. No. 9,613.442, PCT application no. US18/52175, and U.S. Provisional Patent Application No. 62/562,138 allow for accurate reconstruction of such volumetric density information using a reduced number of X-ray images of a sample relative to other methods. In particular, the reduced view and sparse view reconstruction methods described in those patents and patent applications, permit the generation of clinical-quality volumetric density information for explanted breast tissue or other target tissue sample using less than 300 individual X-ray images of the sample, or less than 100 individual X-ray images of the sample. This reduction in the number of X-ray images needed for reconstruction can lead to a reduction in the overall scan time to less than ten minutes, or less than 5 minutes.

Such an imaging system can be configured to create volumetric density information for a sample using a micro-CT imager or other X-ray based tomographic technology. However, such an imaging system could include additional or alternative imaging technologies, e.g., magnetic resonance imaging, volumetric fluorescence imaging, ultrasound imaging, far-ultraviolet imaging, spontaneous emission imaging (e.g., positron-emission imaging), or some other form of volumetric imaging, or some combination of modalities. Indeed, precise automated specimen handling described herein (e.g., using standardized sample receptacles with registration features and/or imaging fiducials) could facilitate the automated imaging of a sample using multiple imaging modalities. The lack of human intervention in the sample handling between imaging modalities could improve registration of data from multiple different imaging modalities by reducing the amount of sample motion or deformation that may occur between performances of the multiple different imaging modalities.

III. EXAMPLE VISUALIZATIONS OF VOLUMETRIC TISSUE SAMPLE IMAGING DATA

A variety of different methods could be used to generate volumetric density information for a tissue sample. For example, a micro-CT imager can be used to generate X-ray radiopacity density information, an MRI imager can be used to generate hydrogen atom or MRI contrast density information, etc. In order to use such volumetric density information to, e.g., inform the sectioning of the tissue sample to facilitate pathological analysis of the tissue, to determine whether a revision surgery is indicated, etc. it is generally advantageous to render, from the volumetric density information, one or more two-dimensional images of the sample. Such two-dimensional images can include high-resolution cross-sectional images of slices through the sample, e.g., slices through the sample that are parallel to the standard coronal, sagittal, and/or transverse planes of the sample according to the orientation of the sample within a patient's body. Two-dimensional images can also include perspective views of the sample. Such perspective views could be useful to illustrate the orientation and location of high-resolution cross-sectional images relative to the sample. Additionally, such perspective views may show, in three-dimensional space, the location of tumors, staples, wires, or other substances or structures of interest within the tissue sample.

As described above, such images, rendered from volumetric imaging data of the tissue sample, may be used to identify regions of interest and/or the location/angle of target sections through the sample in connection with the embodiments described above. The visualization and imaging data manipulation methods described in this section may be used in combination with the methods above in order to generate image or other data to project onto a tissue sample, to identify the locations and angles of sections to make through a tissue sample in order to optimally analyze the sample, to indicate the location/angle of a sectioning tool relative to a tissue sample, to select a location/angle relative to a tissue sample to which to control a sectioning tool, or to facilitate some other functionality described above. Additionally or alternatively, the visualization and imaging data manipulation methods described in this section may be used separately (e.g., by a radiologist) to identify staples, tumors, wires, accumulations of a contrast agent, ducts, blood vessels, calcifications, or other regions of interest within the volumetric imaging data for a tissue sample. Indications of such identified regions of interest (e.g., segmentation maps indicating the location, extent, and/or geometry of such regions) may then be provided to a pathologist's workstation in order to, e.g., identify the location and/or angle of one or more target sections through the tissue sample.

Standard radiology workstations often provide indications of such volumetric imaging information in a four-pane interface, with a first pane providing a perspective view of the sample and the other three panes providing cross-sectional views through the sample parallel to the coronal, sagittal, and transverse planes, respectively. This can be beneficial in providing the radiologist (or pathologist or other healthcare professional using the systems or methods described herein) with maximal information for assessing whether a tumor or other target tissue has been fully excised, or if that target tissue likely has not (e.g., due to the target tissue extending to, or proximate to, a margin of the explanted tissue sample). Such an information-rich display is possible because the radiologist's reading room or other workspace is not likely to be space-limited, and the radiologist is unlikely to be moving between the workstation and other tasks.

The user interface embodiments described herein provide a variety of improvements directed toward providing useful information to a surgeon, pathologist, or other healthcare provider in an intuitive manner. These embodiments include improved user interfaces to assist in analyzing and displaying volumetric data. In some examples, a user interface is provided by a computing system (e.g., an imaging system) that operates an imager to generate scan data for a sample, that reconstructs volumetric density information from the scan data, and that renders two-dimensional images and/or generates other analyses based on the volumetric density information. However, such improved user interfaces can also be provided by a pathologist's workstation, a remote control and display unit for an imaging system and/or sample sectioning and analysis system, or some other interface system that does not operate to reconstruct volumetric density information for a sample or to render two-dimensional images therefrom.

Figure 4A:
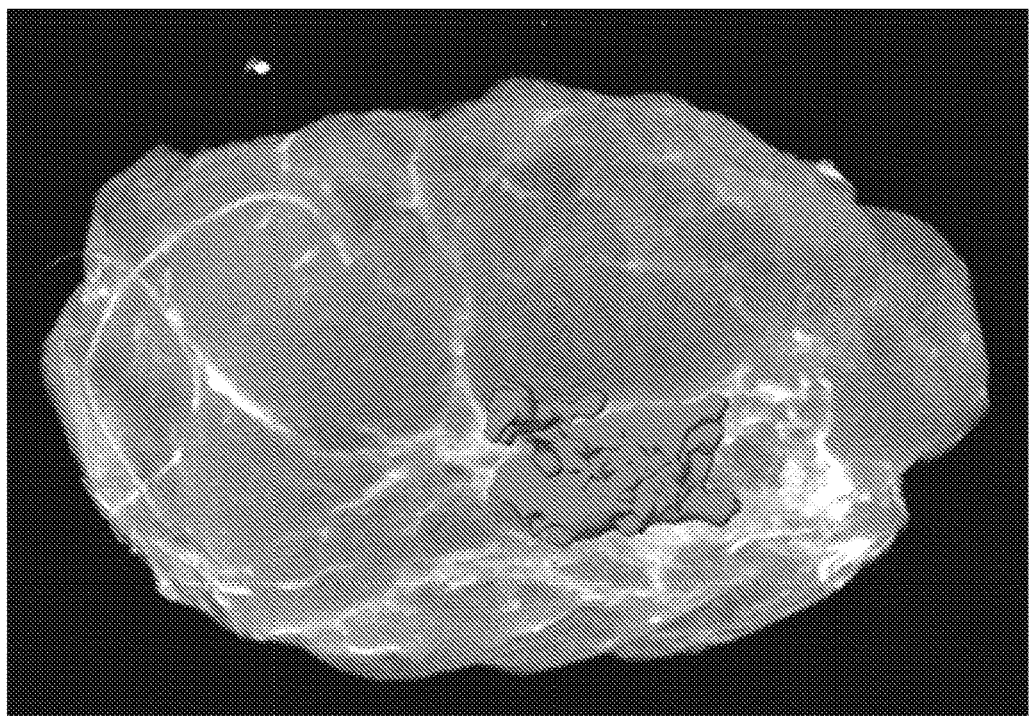
FIG. 4A depicts an example display of volumetric data related to a target sample.

In a first example embodiment, a perspective view of the sample (e.g., a perspective representation of volumetric density information for the sample) can be provided with the location and extent of a tumor or other region of interest indicated. This is illustrated in FIG. 4A, which shows a three-dimensional render of a segmentation map of a tumor within a sample superimposed on a perspective view of the sample. As shown in FIG. 4, the perspective view of the sample includes a projection of the volumetric density information, however, alternative perspective representations of a sample are possible. For example, the perspective representation of the sample could include a render of an outside surface of the sample, with the shape of the outside surface determined from the volumetric density information for the sample. In another example, the perspective representation of the sample could be separated according to the location and/or angle of one or more target sections through the sample, to simulate the appearance of the sample if it were to be sectioned through the target section(s).

A segmentation map for tumors, staples, or other regions of interest within a sample could be generated in a variety of ways. In some examples, an automated algorithm could generate the segmentation map. This could include applying a density threshold to the volumetric density information (e.g., to segment staples, wire, or other high-density content within the sample), applying a trained neural network, or performing some other process on the volumetric density information. In some examples, the segmentation map could be generated by a pathologist or other healthcare professional (e.g., a radiologist). For example, the pathologist could annotate the extent of a tumor or other structure of interest within a tissue sample by, e.g., indicating the extent of the structure of interest in one or more two-dimensional cross-sectional images of the sample. A pathologist could be augmented by one or more automated segmentation methods. For example, an automated method could generate an estimated segmentation map which the pathologist could then edit (e.g., by dragging the edges of the segmentation map to expand or contract the volume of the sample that is included within the segmentation map). In another example, an automated method could generate a number of possible segmentations, and a pathologist could select the 'best' one.

Figure 4B:
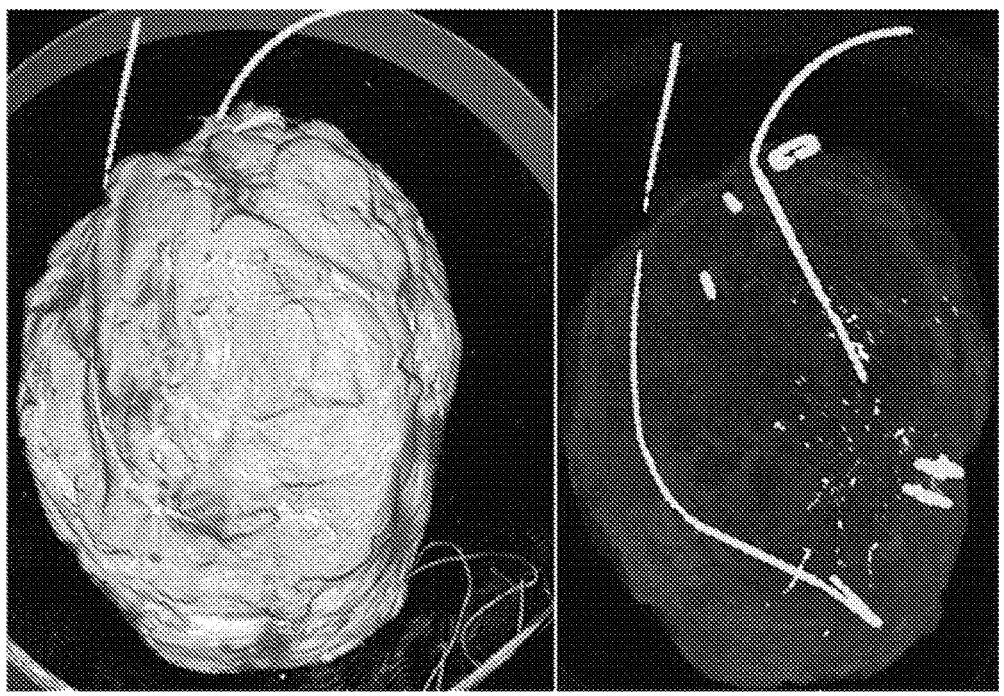
FIG. 4B depicts an example display of volumetric data related to a target sample.

Multiple different tumors, staples, wires, or other objects or sets of objects within a sample could be associated with respective different segmentation maps and/or corresponding regions of interest. A user interface could then provide a user with the ability to selectively blank certain contents of the sample from view by selecting or de-selecting the corresponding segmentation maps. FIG. 4B shows an example of such functionality. On the left, FIG. 4B shows a perspective view (a three-dimensional rendering) of contents of a sample. The contents include a number of metal staples, wires, and other objects that have been added to the sample (e.g., to facilitate orientation of the sample relative to a patient's body). On the right, FIG. 4B shows a perspective view of only the metal objects and calcifications within the tissue (omitting, among other things, the soft tissues having densities less than the density of the calcifications). A user selecting or deselecting individual objects or other contents within a sample for display in the manner could include clicking on or otherwise interacting with buttons of a user interface that are associated with respective contents of the sample, clicking on or otherwise interacting with portions of a display that are displaying contents of the sample, or interacting with a user interface in some other manner.

Figure 5:
FIG. 5 depicts an example display of volumetric data related to a target sample.

It can be advantageous to color-code the surface of a displayed segmentation map according to the distance of portions of the segmentation map to the nearest margin of the tissue sample. Such a display has the benefit of quickly and intuitively indicating to a pathologist where the target tissue is more (or less) likely to extend beyond the margin of the removed tissue and thus to remain, in part, within a patient's body. This is illustrated in FIG. 5, which shows a color-coded perspective view of a segmentation map of a tumor superimposed within a render of the outside surface of the sample that contains the tumor. Such a color coding can be determined, for each point on the surface of the segmentation map, by determining the respective distance to a respective nearest point on the determined outside surface of the target sample. This could be done after a pathologist (or other healthcare professional) has created, updated, or modified the segmentation map. The color-coding thus determined could be projected onto or otherwise indicated relative to the tissue sample (e.g., via a display of a head-mounted display or other augmented reality system) in order to inform sectioning of the tissue sample.

It can be advantageous to colorize the outside of a three-dimensional rendering of a sample so that it superficially resembles the visual-light appearance of the sample. Such coloring can improve a pathologist's intuition about the orientation and composition of the sample and aide them interacting with imaging data related to the sample. However, it can be difficult to generate visible-light imagery of the outside surface of a sample and then to register that imagery with the volumetric density information generated from the sample. Instead, a method can be used that uses the density information of the sample near the surface to inform the coloration of the outside surface of the sample when represented in a perspective view. Lower-density areas of the volumetric density information can result in darker-colored areas of the outside surface (e.g., dark pink, orange, yellow, or red), while higher-density areas of the volumetric density information can result in lighter-colored areas of the outside surface (e.g., white. light pink, light yellow, or light orange). This approximates the relationship between the color of common explanted tissue samples and their X-ray density. The difference between the color of the high-density regions and the color of the low-density regions could be less than 5%. Especially high-density areas of the volumetric density information, which likely correspond to metal staples, wires, or other artificial elements inserted into the sample, can result in a specified color, e.g., white or gray, to indicate the presence of a high-density artificial object in the sample. Such a method could additionally or alternatively be used to color two-dimensional cross-sectional images through the volumetric imaging data (e.g., as shown in FIG. 3C).

Figure 6A:
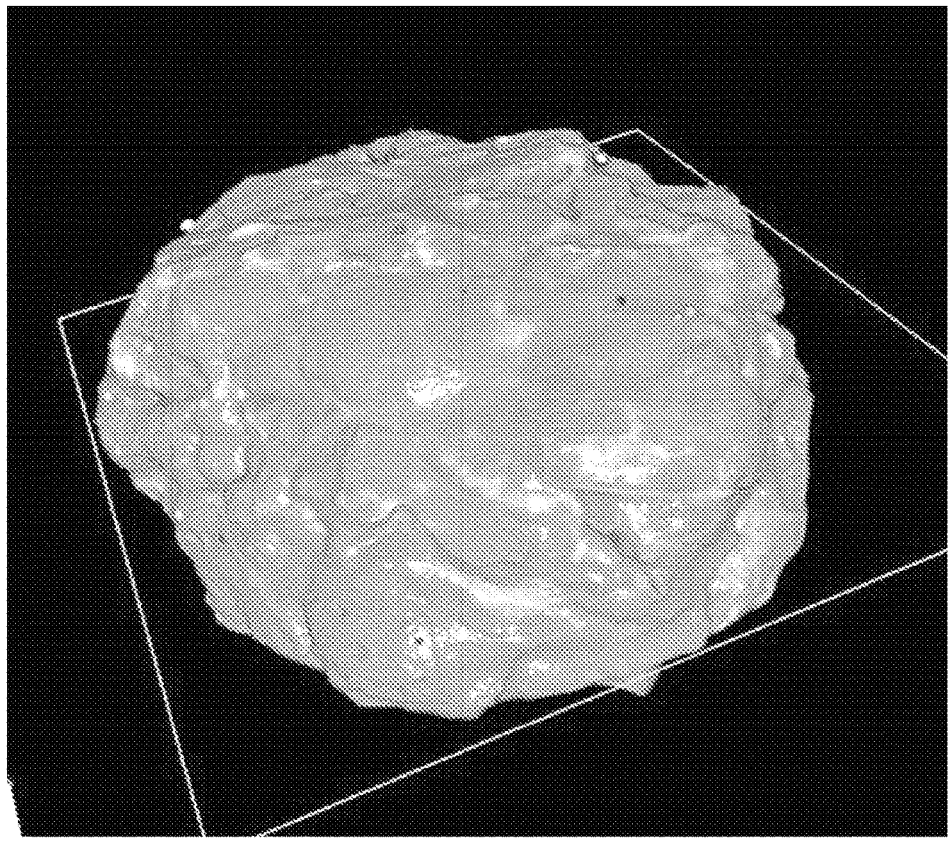
FIG. 6A depicts an example display of volumetric data related to a target sample.

An example of such a surface color-coding is illustrated in FIG. 6A. The mapping between density and surface coloration could be a linear function or a nonlinear function. For example, determining a color for the particular point on the outside surface of a sample could include linearly or nonlinearly mapping the density of a portion of the volumetric density information that is proximate to the particular point to a range of colors. The density-to-color mapping could be based on a piecewise function. For example, a first range of densities (e.g., a range of densities corresponding to the density of soft tissues in a sample) could be mapped linearly across a range of colors (e.g., light orange to white) while densities greater than the first range of densities (e.g., densities corresponding to stapled, wires, or other metallic or other high-density non-tissue substances) are mapped to a single color (e.g., grey). The mapping of densities to colors could be normalized, e.g., to a histogram or other percentile determination of densities represented within a set of volumetric density information for a sample. For example, a range of densities from the 25% to the 75% of densities within a sample could be mapped linearly (or nonlinearly) to a first range of colors (e.g., light red to white) while densities above the 75% could be mapped to grey or to some other color indicative of staples, wires, or other metallic or otherwise non-organic materials.

In practice, a surgeon may insert wires, sutures, staples, or other artifacts to indicate the orientation of a sample, or may add ink to the surface of the sample to indicate orientation. However, these methods may still result in the pathologist and surgeon having different understandings of the orientation of the sample. Such a difference can result in poorer surgical outcomes; if the pathologist and surgeon differ with respect to their understandings of the orientation of a sample, the pathologist's recommendations (e.g., diagnosis as to the success of a procedure in fully removing a tumor or other target) may not be accurate.

Figure 6B:
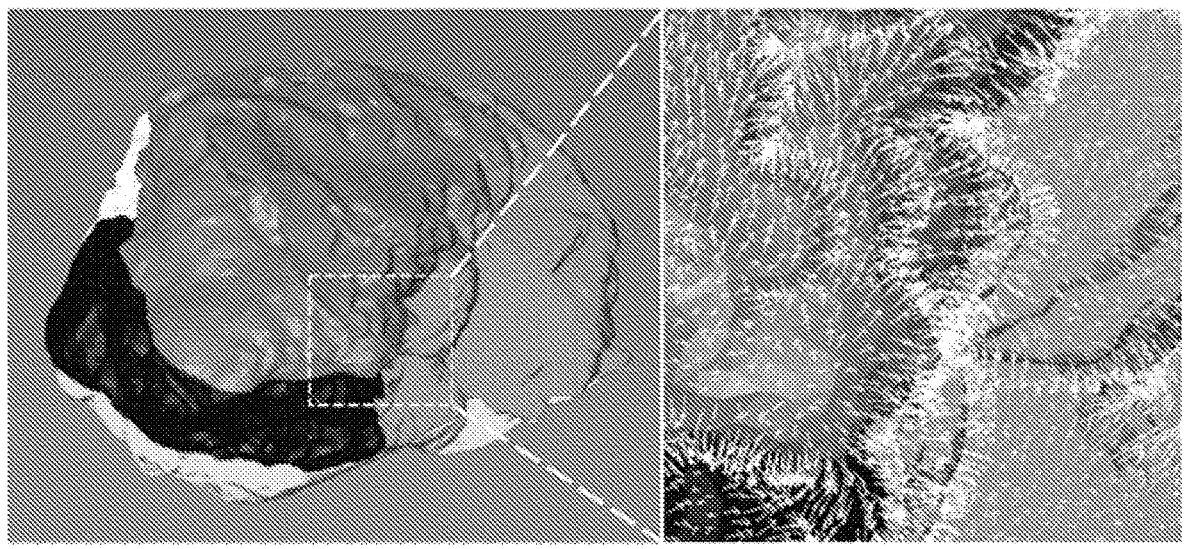
FIG. 6B depicts an example display of volumetric data related to a target sample.

Thus, it can be advantageous to colorize the outside of a three-dimensional rendering of a sample based on a surgeon's understanding of the orientation of the sample. Providing such a colorization to a pathologist can improve the pathologist's understanding of the sample's orientation so that any recommendations made by the pathologist are more likely to be accurate or correct. An example of such a surface color-coding is illustrated in FIG. 6B. Each of the six cardinal directions in three-dimensional space (anterior, posterior, medial, lateral, ventral, and dorsal) corresponds to a respective color. Such 'virtual inking' can also assist the pathologist in physically inking the imaged sample in a manner that more accurately corresponds to the actual orientation of the sample within a patient's body.

Orientation-based colorization of an outside surface of a target sample could be performed in a variety of ways. For example, a surface normal could be determined for a plurality of locations on the outside surface and the surface normals then used to determine the color-coding of the outside surface. This could include mapping the surface normals to colors according to which of the cardinal directions they are closest to, and then performing hole-filling, region-expanding, or other filtering techniques to generate a final surface coloring. Additionally or alternatively, a surgeon could virtually 'paint' the surface manually, or manually modify an automatically-generated surface coloration. The surgeon could set or modify the orientation of the volumetric density information relative to a three-dimensional space, and the surface coloration could be generated or re-generated based on the relative orientation. This surface coloration, which now corresponds to the surgeon's understanding of the orientation of the sample, could then be provided to a pathologist so as to ensure that the pathologist and surgeon are operating from the same understanding of the orientation of the sample.

Figure 7:
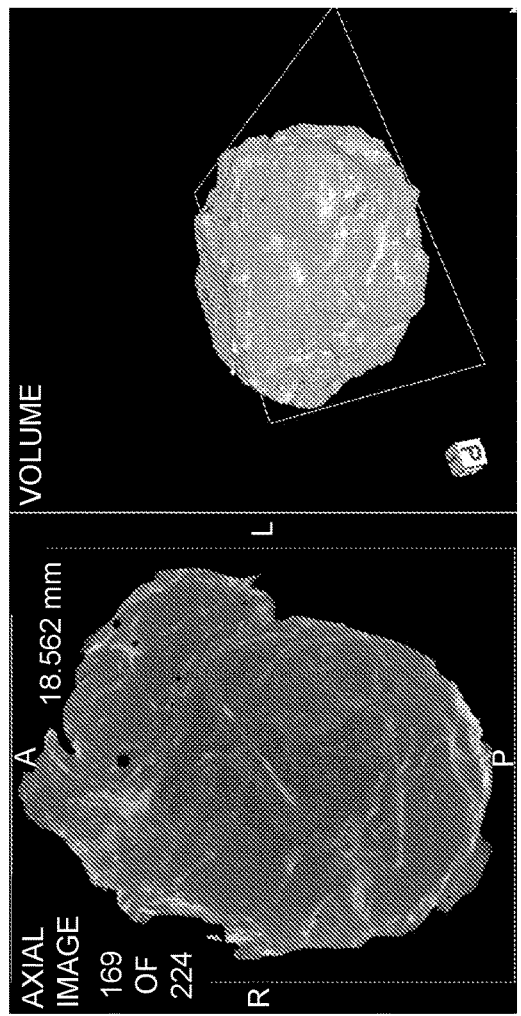
FIG. 7 depicts elements of an example user interface for displaying multiple views of volumetric data related to a target sample.

To improve clinical outcomes, an improved user interface is provided for presenting imaging data to a surgeon or other healthcare professional in a concise, informative, and easy-to-use fashion. FIG. 7 illustrates, by way of example, features of this improved user interface. The user interface has two primary panes, with the right pane providing a perspective representation of the volumetric density information for a sample (a simulated color render of the outside surface of the sample) and the left pane providing a high-resolution two-dimensional image of the sample according to a cross-sectional view through a specified view point within the sample and orthogonal to a first axis in a three-dimensional space. The three-dimensional space represents the orientation of the sample relative to a patient's body, and can be adjusted by the user (as described in greater detail below).

Figure 8A:
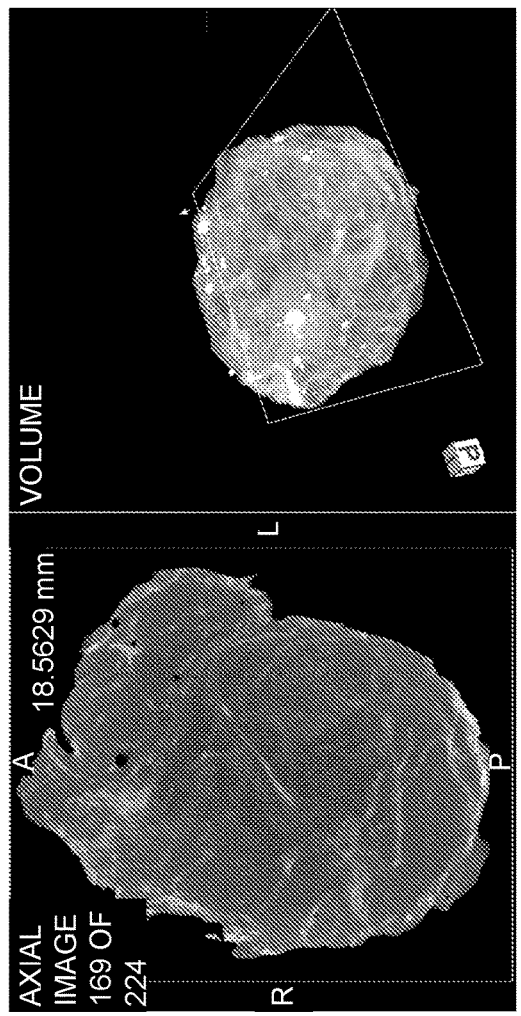
FIG. 8A depicts elements of an example user interface for displaying multiple views of volumetric data related to a target sample.

The particular perspective view of the sample provided in the right pane can be controlled by a user in a variety of ways. For example, a user could click and drag to rotate the perspective view about an axis, or use a two-finger gesture to zoom in or out. Alternatively, buttons arranged as a quartet of directional arrows or some other user interface element (not shown) could be used to accomplish such changes. The type of perspective view (e.g., surface coloration according to orientation, projected density view with internal structures indicated, etc.) could be modified by pressing buttons on the user interface, engaging a drop-down menu, or by some other means. For example, the user interface could be used (e.g., by clicking or otherwise interacting with a button, not shown) to switch between the simulated surface render view depicted in FIG. 7 to a maximum-density projection view, as depicted in FIG. 8A.

Figure 8B:
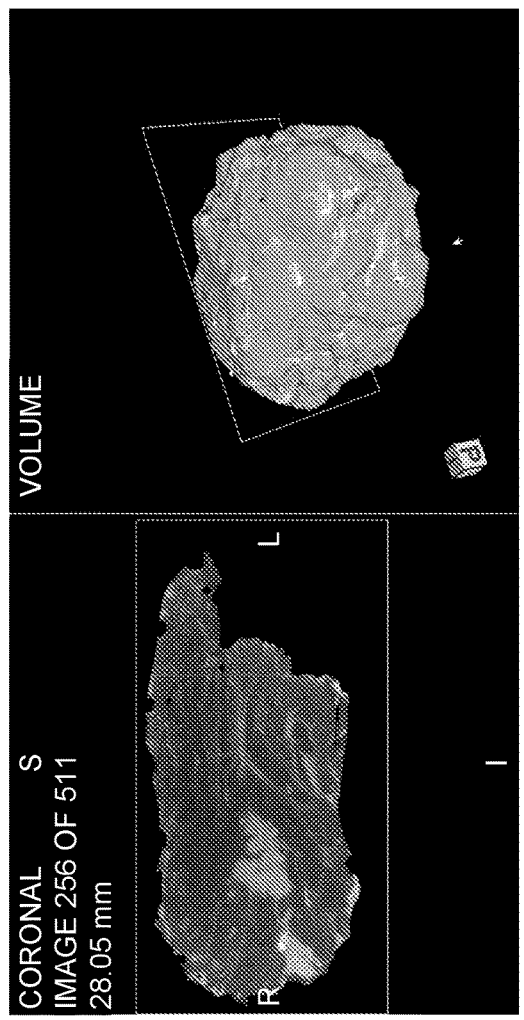
FIG. 8B depicts elements of an example user interface for displaying multiple views of volumetric data related to a target sample.

The location of the specified view point and the orientation of the two-dimensional image provided in the left pane can be controlled by a user in a variety of ways. For example, the plane of the image could be changed between the three major anatomical planes by pressing buttons on the interface. The location of the view point within the sample could be modified by pressing buttons (not shown), by clicking points of interest on the perspective view, or by engaging in some other control behavior. For example, the user interface could be used (e.g., by clicking or otherwise interacting with a button, not shown) to switch between a view through a first anatomical plane (e.g., the axial plane), as depicted in FIG. 7, to through a second anatomical plane (e.g., the coronal plane), as depicted in FIG. 8B.

Figure 8C:
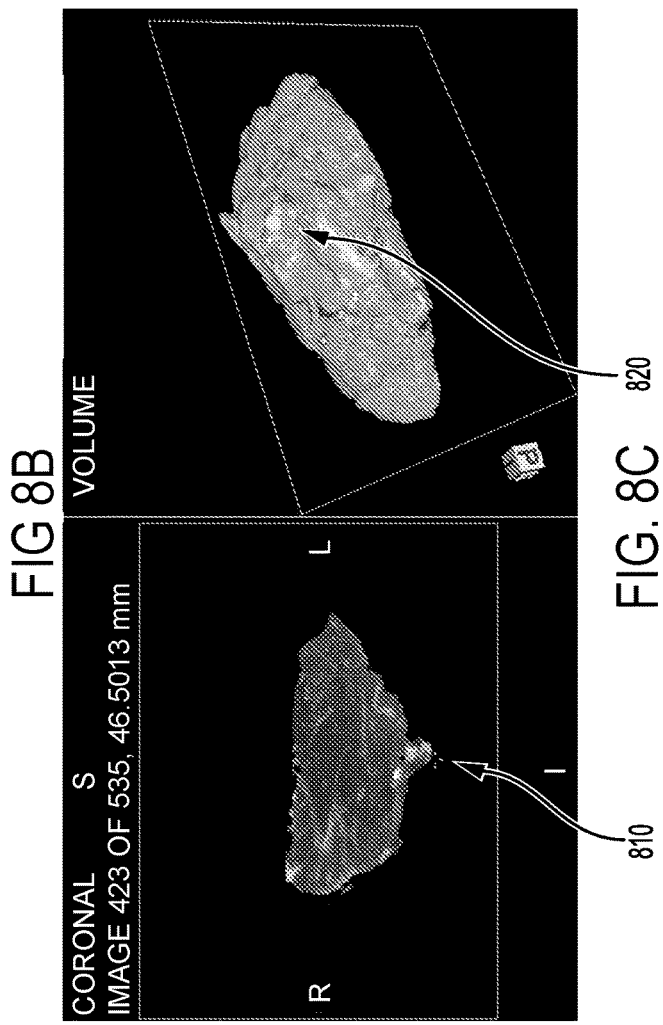
FIG. 8C depicts elements of an example user interface for displaying multiple views of volumetric data related to a target sample.

The orientation of the volumetric density information relative to the three-dimensional space can be adjusted by the user by clicking or otherwise interacting with a user interface a button (e.g., a "re-orienter" button, not shown) and then dragging the perspective view until the orientation of the sample, as shown in the perspective view, matches the user's desired orientation. Once such a re-orientation has occurred, the cross-sectional image shown in the left pane could be updated to correspond to the change in orientation (e.g., so that the two-dimensional image in the left pane corresponds to one of the three principal anatomical planes according to the updated three-dimensional space). This is illustrated, by way of example, in FIG. 8C, which depicts updates to the display of FIG. 8B following such a re-orientation. The updated orientation could also result in updates in other displays, e.g., updated two-dimensional cross-sectional images presented to a radiologist using another system, updated surface coloration of a perspective view of the sample to reflect the change in the orientation of the three-dimensional space relative to the sample, or updating some other display or system.

A user indicating a point in the cross-sectional view could result in the location of the indicated point, within the three-dimensional space of the sample, being indicated in the perspective view of the sample. This is illustrated by way of example in FIG. 8C. A user has indicated a point of interest 810 within the cross-sectional view of the left pane and the location of the indicated point, within the perspective view of the right pane, has been indicated 840. The location of this indicated point in the three-dimensional space can be updated as the user rotates the perspective view, zooms the perspective view, or otherwise causes the perspective view to change.

The location, relative to the sample, of the view point through which the left pane displays a cross-sectional image may be controlled in a variety of ways. The view point could be moved in a direction perpendicular to the plane of the image by clicking buttons on the user interface, by dragging the left pane (e.g., dragging upward resulting in movement of the view point 'toward' the user, dragging downward resulting in movement of the view point 'away from' the user), or by interacting with the left pane in some other manner. In some examples, a user could indicate a point of interest on the perspective view of a sample in the right pane, and this could result in the location of the view point changing to the indicated point of interest. For example, if the user clicked on a region that contains a calcification or other increased-density region or object, the view point could be changed to correspond to the location of the calcification.

Figure 8D:
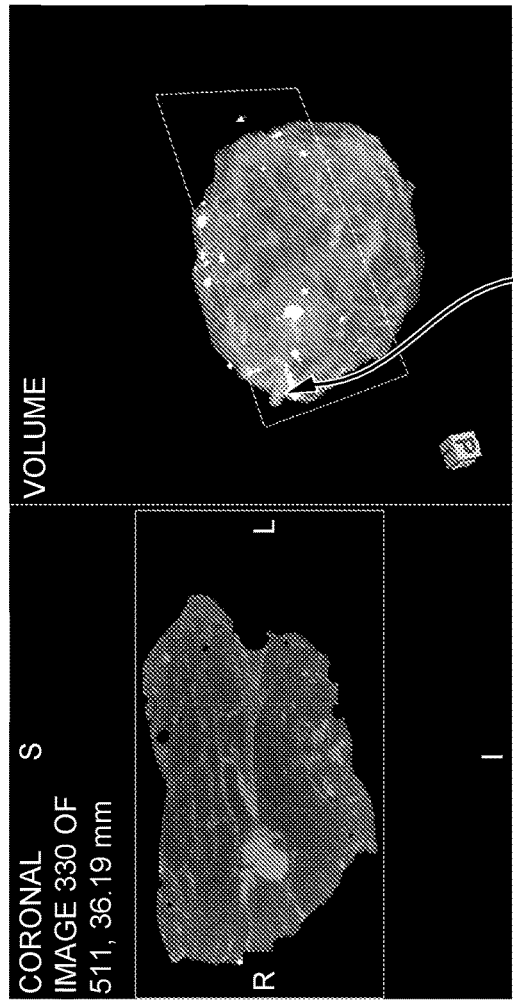
FIG. 8D depicts elements of an example user interface for displaying multiple views of volumetric data related to a target sample.
Figure 8E:
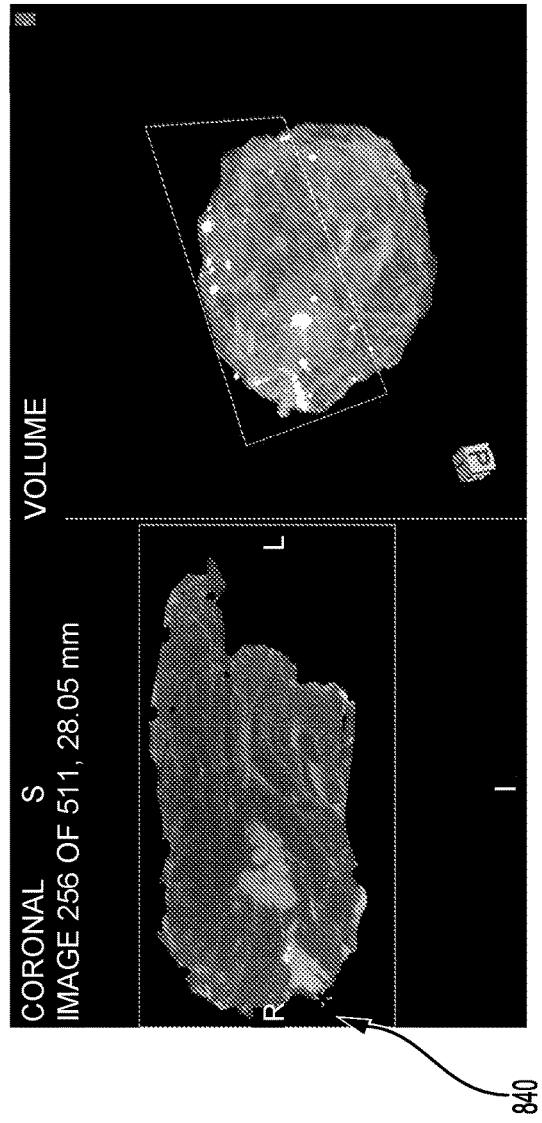
FIG. 8E depicts elements of an example user interface for displaying multiple views of volumetric data related to a target sample.

This is illustrated by way of example in FIGS. 8D and 8E. In FIG. 8D, a user has indicated a point of interest 830 within the perspective representation of the sample. In response, the left pane view has changed, In FIG. 8E, to provide a cross-sectional view through an updated view point corresponding to the point of interest. Additionally, the location of the updated view point, within the updated cross-sectional image, has been indicated 840 in the left pane display A variety of methods could be used to determine the location of the updated view point based on such a user input. In some examples, the location of a highest-density region within the sample and proximate to the region indicated by the user input could be determined. This could include (i) receiving, via the user interface, an indication of the point of interest within the perspective representation of the volumetric density information, (ii) determining, based on the indicated point on the display, a corresponding columnar portion of the volumetric density information; and (iii) determining the location, within the three dimensional space, of the point of interest by determining the location of a maximal-density region within the columnar portion of the volumetric density information.

Note that the description of certain user interactions and/or display of certain information as corresponding to a 'left pane' or a 'right pane' of a user interface is intended to illustrate non-limiting example embodiments. Such functionality could be distributed oppositely, or, indeed, to 'upper' and 'lower' panes of a two-pane interface. Further, one of skill in the art will appreciate that many of the display modalities, visualizations, and user interface functions described above may be applied to user interfaces having more than two panes, e.g., to a traditional four-pane radiologist's workstation user interface.

IV. EXAMPLE SYSTEMS

Computational functions described herein may be performed by one or more computing systems. Such computational functions may include functions to operate an imager to generate scan data for a target sample, functions to reconstruct volumetric density information from such scan data, functions to render cross-sectional, perspective, or other two-dimensional views from the volumetric density data, functions to project an indication of scan-related data onto a tissue sample, functions to provide an indication of scan-related data onto a display of a head-mounted device such that it appears from a user's perspective on the tissue sample, functions to drive a sectioning apparatus to a desired location/angle relative to a tissue sample and/or to section the tissue sample, and/or user interface functions. Such a computing system may be integrated into or take the form of a computing device, such as a portable medical imaging system, a remote interface for such an imaging system, a pathologist's workstation, a tissue analysis and/or sectioning table or workstation, a tablet computer, a laptop computer, a server, a cloud computing network, and/or a programmable logic controller.

Figure 9:
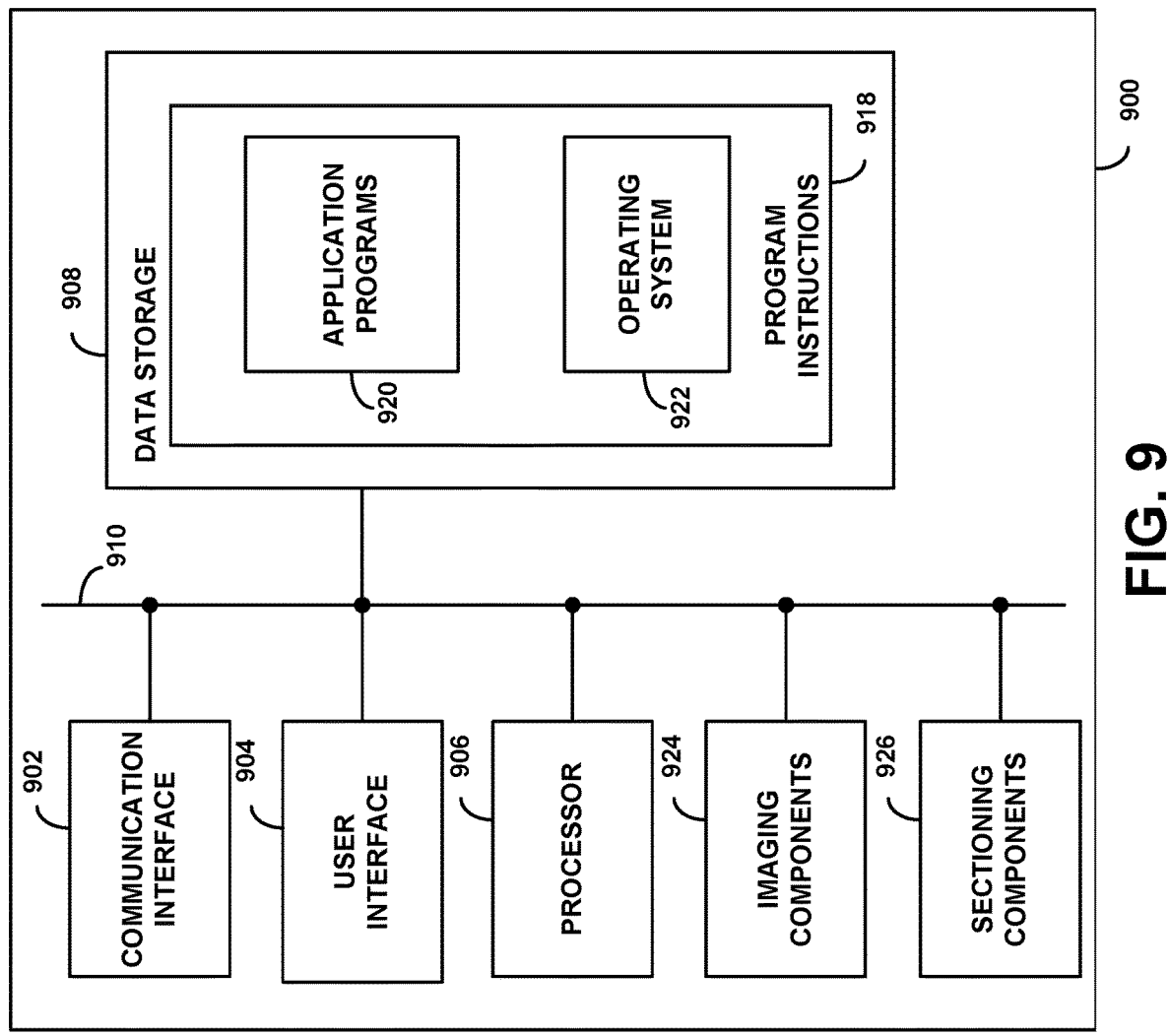
FIG. 9 is a simplified block diagram showing some of the components of an example system.

For purposes of example, FIG. 9 is a simplified block diagram showing some of the components of an example computing device 900 that may include components for providing indications of scan-related data onto a tissue sample (e.g., via a projector, head-mounted display, or other user interface components 904), for detecting the location/angle of a sectioning jig or other element(s) of sectioning components 926, and/or for controlling the location/angle of a sectioning jig or other element(s) of sectioning components 926. Alternatively, an example computing device may lack such components and provide indications of imaging data onto a tissue sample and/or detect or control the location/angle of a sectioning tool via some other means (e.g., via the internet or some other network or other communications interface).

The computing device 900 may also include imaging components 924 for obtaining imaging data for such a tissue sample. Imaging components 924 may include a micro-CT imager, an MRI imager, and/or some other components configured to provide information indicative of volumetric density information for a sample. Alternatively, an example computing device may lack such components and receive scan information via some other means (e.g., via the internet or some other network or other communications interface).

As shown in FIG. 9, computing device 900 may include a communication interface 902, a user interface 904, a processor 906, data storage 908, imaging components 924, and sectioning component 926, all of which may be communicatively linked together by a system bus, network, or other connection mechanism 910.

Communication interface 902 may function to allow computing device 900 to communicate, using analog or digital modulation of electric, magnetic, electromagnetic, optical, or other signals, with other devices, access networks, and/or transport networks. Thus, communication interface 902 may facilitate circuit-switched and/or packet-switched communication, such as plain old telephone service (POTS) communication and/or Internet protocol (IP) or other packetized communication. For instance, communication interface 902 may include a chipset and antenna arranged for wireless communication with a radio access network or an access point. Also, communication interface 902 may take the form of or include a wireline interface, such as an Ethernet, Universal Serial Bus (USB), or High-Definition Multimedia Interface (HDMI) port. Communication interface 902 may also take the form of or include a wireless interface, such as a Wi-Fi, BLUETOOTH®, global positioning system (GPS), or wide-area wireless interface (e.g., WiMAX or 3GPP Long-Term Evolution (LTE)). However, other forms of physical layer interfaces and other types of standard or proprietary communication protocols may be used over communication interface 902. Furthermore, communication interface 902 may comprise multiple physical communication interfaces (e.g., a Wi-Fi interface, a BLUETOOTH® interface, and a wide-area wireless interface).

In some embodiments, communication interface 902 may function to allow computing device 900 to communicate, with other devices, remote servers, access networks, and/or transport networks. For example, the communication interface 902 may function to transmit and/or receive an indication of image information, to transmit an indication of imaging-related data that can then be projected onto or otherwise displayed relative to a tissue sample, to transmit an indication of a location and/or angle, relative to a tissue sample, to which a sectioning tool may be driven, or some other information. For example, the computing device 900 could be a pathologist's workstation located in a pathologist's office, remote from one or more pathology labs wherein sample sectioning and preparation occur, and the remote system could be a projector, augmented reality system, automated sample preparation system, or other system configured to facilitate analysis and manipulation of tissue samples as described herein.

In some examples, the computing device 900 could include a volumetric imaging system (e.g., a micro-CT imager) and computational resources for reconstructing volumetric density information from scan data, for identifying regions of interest and/or suggested section locations/angles from the volumetric density information, for rendering images of tissue samples based on the volumetric density information (e.g., perspective views, simulated two-dimensional slices through the sample, etc.), or for performing some other computational tasks. Such computational resources could include one or more GPUs or other processors specialized for reconstruction, rendering, or other image-processing tasks as described herein. Such a computing device 900 could be in communication with a terminal device (e.g., a workstation, a tablet computer, a head-mounted display, an automated sectioning tool, a thin client) and could provide rendered images to such a terminal in response to user inputs indicative of such rendered images. For example, a user input to a user interface (e.g., keyboard, touchscreen, mouse, head tracker of a head-mounted display) could cause the terminal device to send, to the computing device 900, a request for imaging data related to the user input (e.g., a request for an updated two-dimensional cross-sectional image through a tissue sample based on a user input updating the location/angle of a corresponding section though the tissue sample). The computing device 900 could then, in response to the request, transmit to the terminal device some information indicative of the requested data (e.g., one or more two-dimensional images, a wireframe/segmentation map or other simplified representation of the volumetric density information). Such operations could allow the terminal device to be lower cost, lighter, smaller, or otherwise improved to facilitate interaction therewith by a pathologist or other healthcare professional while maintaining access to the imaging and processing resources of the computing device 900.

User interface 904 may function to allow computing device 900 to interact with a user, for example to receive input from and/or to provide output to the user. Thus, user interface 904 may include input components such as a keypad, keyboard, touch-sensitive or presence-sensitive panel, computer mouse, trackball, joystick, microphone, and so on. User interface 904 may also include one or more output components such as a display screen which, for example, may be combined with a presence-sensitive panel. The display screen may be based on CRT, LCD, and/or LED technologies, or other technologies now known or later developed. User interface 904 may also be configured to generate audible output(s), via a speaker, speaker jack, audio output port, audio output device, earphones, and/or other similar devices.

In some embodiments, user interface 904 may include a display that serves to provide, relative to a tissue sample, indications of regions of interest or other imaging-related information to a user (e.g., by projecting onto a tissue sample an indication of the location of a tumor within the sample and/or an indication of a section to cut through the tissue sample according to the methods described herein). Additionally, user interface 904 may include one or more buttons, switches, knobs, and/or dials that facilitate the configuration and operation of the imaging components 924, the operation of the sectioning components 926, or to configure some other operation of the computing device 900. It may be possible that some or all of these buttons, switches, knobs, and/or dials are implemented as functions on a touch- or presence-sensitive panel.

Processor 906 may comprise one or more general purpose processors—e.g., microprocessors—and/or one or more special purpose processors—e.g., digital signal processors (DSPs), graphics processing units (GPUs), floating point units (FPUs), network processors, or application-specific integrated circuits (ASICs). In some instances, special purpose processors may be capable of image processing, image registration and/or scaling, and tomographic reconstruction, among other applications or functions. Data storage 908 may include one or more volatile and/or non-volatile storage components, such as magnetic, optical, flash, or organic storage, and may be integrated in whole or in part with processor 906. Data storage 908 may include removable and/or non-removable components.

Processor 906 may be capable of executing program instructions 918 (e.g., compiled or non-compiled program logic and/or machine code) stored in data storage 908 to carry out the various functions described herein. Therefore, data storage 908 may include a non-transitory computer-readable medium, having stored thereon program instructions that, upon execution by computing device 900, cause computing device 900 to carry out any of the methods, processes, or functions disclosed in this specification and/or the accompanying drawings.

By way of example, program instructions 918 may include an operating system 922 (e.g., an operating system kernel, device driver(s), and/or other modules) and one or more application programs 920 (e.g., sample scanning functions, reconstruction or rendering functions) installed on computing device 900.

Application programs 920 may take the form of "apps" that could be downloadable to computing device 900 through one or more online application stores or application markets (via, e.g., the communication interface 902). However, application programs can also be installed on computing device 900 in other ways, such as via a web browser or through a physical interface (e.g., a USB port) of the computing device 900.

In some examples, portions of the methods described herein could be performed by different devices, according to an application. For example, different devices of a system could have different amounts of computational resources (e.g., memory, processor cycles) and different information bandwidths for communication between the devices. For example, a first device could be a pathologist's workstation or remote interface that could transmit commands and/or requests for imaging data to another device or server that has the necessary computational resources to perform the reconstruction and/or rendering methods required to generate the requested imaging data, e.g., from CT scan data of a tissue sample. Different portions of the methods described herein could be apportioned according to such considerations.

V. EXAMPLE METHODS

Figure 10:
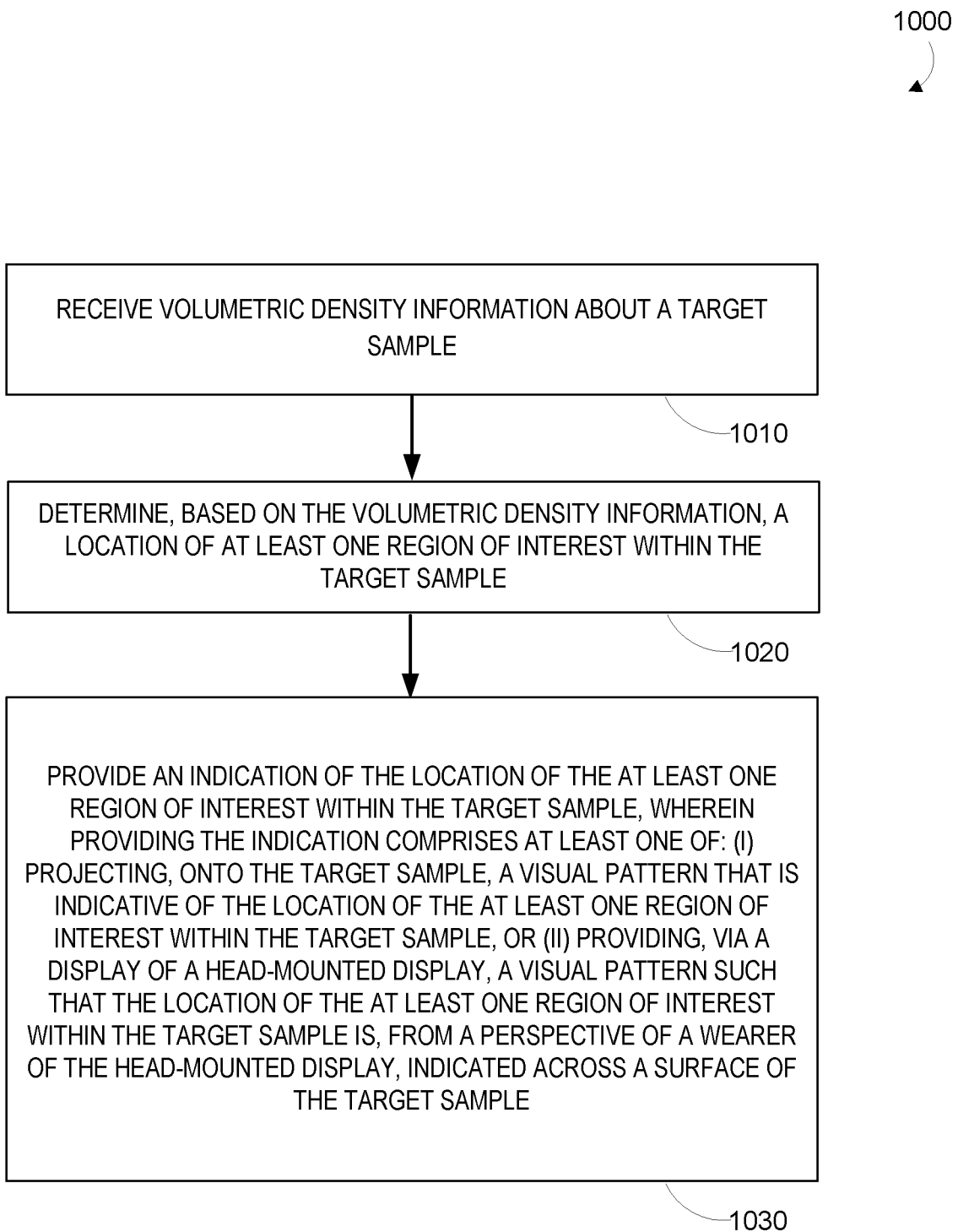
FIG. 10 is a flowchart of a method, according to an example embodiment.

FIG. 10 is a flowchart of a method 1000. The method 1000 includes receiving volumetric density information about a target sample (1010). The method 1000 additionally includes determining, based on the volumetric density information, a location of at least one region of interest within the target sample (1020). The method also includes providing an indication of the location of the at least one region of interest within the target sample, wherein providing the indication comprises at least one of: (i) projecting, onto the target sample, a visual pattern that is indicative of the location of the at least one region of interest within the target sample, or (ii) providing, via a display of a head-mounted display, a visual pattern such that the location of the at least one region of interest within the target sample is, from a perspective of a wearer of the head-mounted display, indicated across a surface of the target sample (1030). The method 1000 could include additional elements or features.

Figure 11:
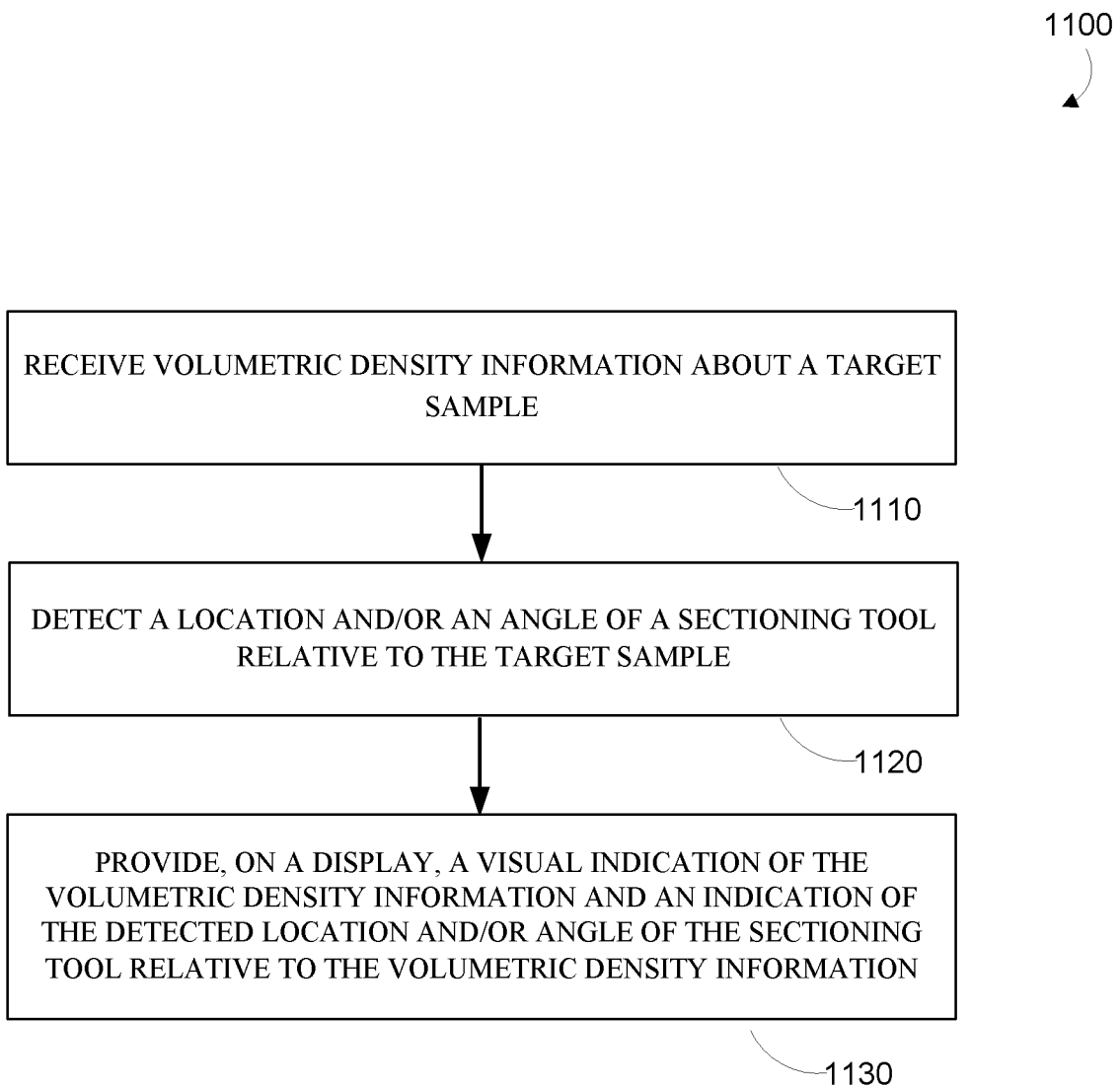
FIG. 11 is a flowchart of a method, according to an example embodiment.

FIG. 11 is a flowchart of a method 1100. The method 1100 includes receiving volumetric density information about a target sample (1110). The method 1100 additionally includes detecting a location and/or an angle of a sectioning tool relative to the target sample (1120). The method 1100 also includes providing, on a display, a visual indication of the volumetric density information and an indication of the detected location and/or angle of the sectioning tool relative to the volumetric density information (1130). The method 1100 could include additional elements or features.

Figure 12:
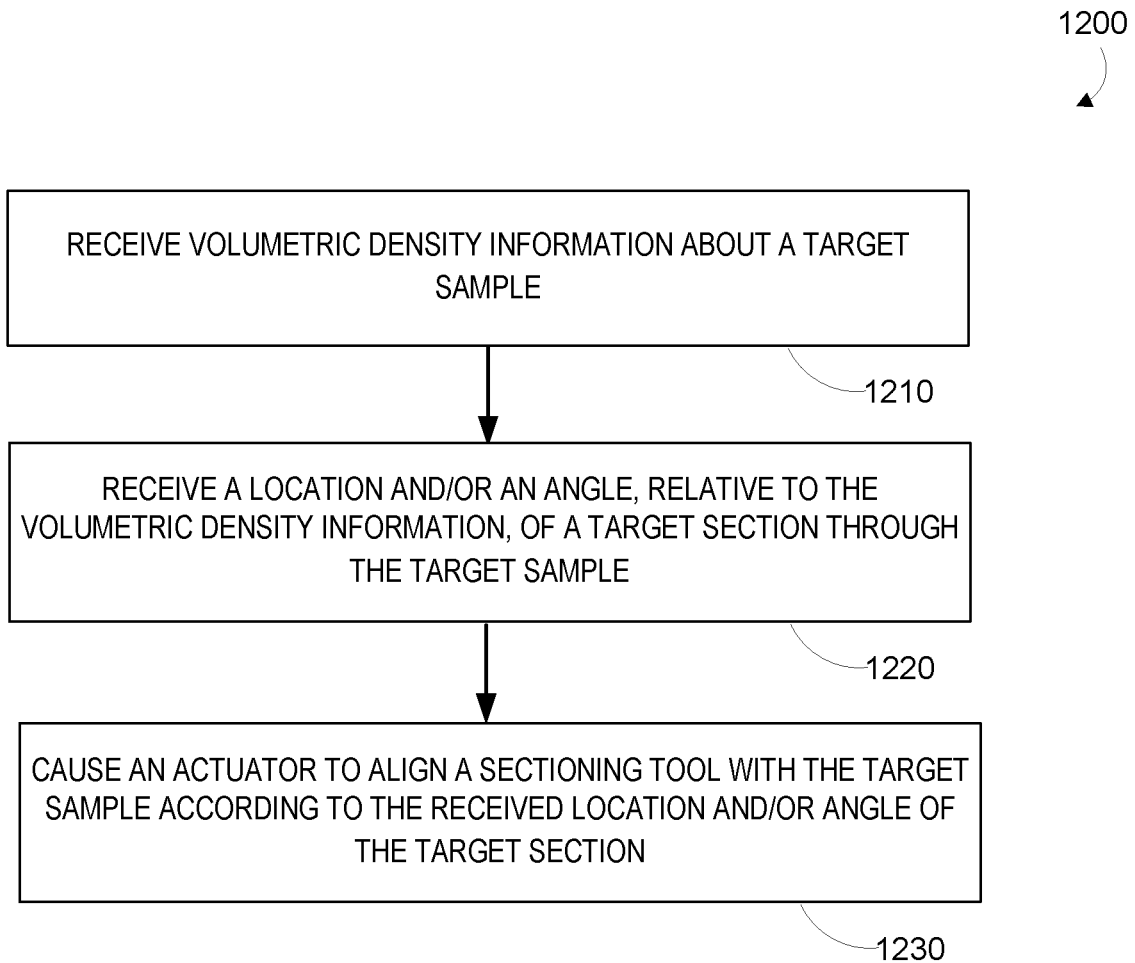
FIG. 12 is a flowchart of a method, according to an example embodiment.

FIG. 12 is a flowchart of a method 1200. The method 1200 includes receiving volumetric density information about a target sample (1210). The method 1200 additionally includes receiving a location and/or an angle, relative to the volumetric density information, of a target section through the target sample (1220). The method 1200 also includes causing an actuator to align a sectioning tool with the target sample according to the received location and/or angle of the target section (1230). The method 1200 could include additional elements or features.

In any of the methods described herein (e.g., methods 1000, 1100, 1200 or other embodiments described herein), the process of obtaining (e.g., "receiving") volumetric density information about a target sample could include a variety of different processes and/or apparatus. In some examples, the volumetric density information could be stored on a hard drive that is accessed to generate imaging data or other information that can be used according to the embodiments described herein. Such stored volumetric density information could be generated near in time and/or space to its use to facilitate sectioning of a sample or could be generated a longer period of time before and/or distance away from the time and place at which the information is used to facilitate sectioning of the sample. For example, the volumetric density information could be generated by operating an X-ray scanner or other volumetric imaging device that is located in an operating room where the tissue sample is removed from a patient. Such volumetric density information could be used by a surgeon and/or radiologist to decide, during the tissue removal procedure, whether additional tissue should be removed from the patient and, if so, from what location(s) within the patient's body. Such volumetric density information could later be used by a pathologist to facilitate sectioning of the explanted tissue sample (e.g., to generate a final diagnosis at to the complete removal of a tumor, the type of stage of a tumor, etc.). Additionally or alternatively, the volumetric density information could be generated by operating an X-ray scanner or other volumetric imaging device that is located in pathology lab where the tissue sample will be sectioned at a time soon before the tissue sample is sectioned. This could be done to ensure that the volumetric density information used to inform sectioning of the tissue sample is 'fresh' and accurately represents the tissue sample at the time of sectioning, as explanted tissue samples can deform, reduce in size, or undergo other changes over time after removal from a body and/or due to sample handling processes.

VI. CONCLUSION

The above detailed description describes various features and functions of the disclosed systems, devices, and methods with reference to the accompanying figures. In the figures, similar symbols typically identify similar components, unless context indicates otherwise. The illustrative embodiments described in the detailed description, figures, and claims are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The embodiments herein are described as being used by pathologists, radiologists, surgeons, and other healthcare professionals to facilitate sectioning or other manipulation or analysis of tissue samples in an image-guided manner and to visualize such image data to select planes through which to section such samples or to otherwise target further manipulations and/or analysis of such samples. However, these are merely illustrative example applications. The embodiments described herein could be employed to image, section, or otherwise manipulate other objects or substances of interest (e.g., plant or animal tissue) and to visualize such image data.

With respect to any or all of the message flow diagrams, scenarios, and flowcharts in the figures and as discussed herein, each step, block and/or communication may represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages may be executed out of order from that shown or discussed, including in substantially concurrent or in reverse order, depending on the functionality involved. Further, more or fewer steps, blocks and/or functions may be used with any of the message flow diagrams, scenarios, and flow charts discussed herein, and these message flow diagrams, scenarios, and flow charts may be combined with one another, in part or in whole.

A step or block that represents a processing of information may correspond to circuitry that can be configured to perform the specific logical functions of a herein-described method or technique. Alternatively or additionally, a step or block that represents a processing of information may correspond to a module, a segment, or a portion of program code (including related data). The program code may include one or more instructions executable by a processor for implementing specific logical functions or actions in the method or technique. The program code and/or related data may be stored on any type of computer-readable medium, such as a storage device, including a disk drive, a hard drive, or other storage media.

The computer-readable medium may also include non-transitory computer-readable media such as computer-readable media that stores data for short periods of time like register memory, processor cache, and/or random access memory (RAM). The computer-readable media may also include non-transitory computer-readable media that stores program code and/or data for longer periods of time, such as secondary or persistent long term storage, like read only memory (ROM), optical or magnetic disks, and/or compact-disc read only memory (CD-ROM), for example. The computer-readable media may also be any other volatile or non-volatile storage systems. A computer-readable medium may be considered a computer-readable storage medium, for example, or a tangible storage device.

Moreover, a step or block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

VII. ENUMERATED EXAMPLE EMBODIMENTS

Embodiments of the present disclosure may thus relate to one of the enumerated example embodiments (EEEs) listed below. It will be appreciated that features indicated with respect to one EEE can be combined with other EEEs.

EEE 1 is a method including: (i) receiving volumetric density information about a target sample; (ii) determining, based on the volumetric density information, a location of at least one region of interest within the target sample; and (iii) providing an indication of the location of the at least one region of interest within the target sample, wherein providing the indication includes at least one of: (a) projecting, onto the target sample, a visual pattern that is indicative of the location of the at least one region of interest within the target sample, or (b) providing, via a display of a head-mounted display, a visual pattern such that the location of the at least one region of interest within the target sample is, from a perspective of a wearer of the head-mounted display, indicated across a surface of the target sample.

EEE 2 is the method of EEE 1, wherein determining the location of at least one region of interest within the target sample includes determining, based on the volumetric density information, a location of at least one of: a staple, a tumor, a wire, an accumulation of a contrast agent, a duct, a blood vessel, or a calcification.

EEE 3 is the method of EEE 1, wherein determining the location of at least one region of interest within the target sample includes: determining, based on the volumetric density information, an outer surface of the target sample; determining, based on the volumetric density information, a segmentation map of one or more volumes of interest within the target sample; and based on the determined outer surface of the target sample and the determined segmentation map, determining a segmentation surface color coding for the segmentation map that color-codes a plurality of points on a surface of the segmentation map according to their respective distances to respective nearest points on the determined outer surface of the target sample, wherein providing the indication of the location of the at least one region of interest within the target sample includes providing an indication of location the segmentation map within the target sample and with the segmentation map colored according to the determined segmentation surface color coding.

EEE 4 I the method of any preceding EEE, further including: receiving a location and/or an angle, relative to the target sample, of a target section through the target sample, wherein providing the indication of the location of the at least one region of interest within the target sample includes providing an indication of the received location and/or angle of the target section within the target sample.

EEE 5 is the method of EEE 4, further including: providing, on a display, a two-dimensional visual depiction of the volumetric density information along the target section through the target sample.

EEE 6 is the method of EEE 5, further including: based on the volumetric density information, determining a cross-sectional color coding for the target section that color-codes a plurality of points across the target section based on the density of respective proximate portions of the volumetric density information, wherein providing, on the display, the two-dimensional visual depiction of the volumetric density information along the target section through the target sample includes providing, on the display, a cross-sectional view of the of the target sample along the target section with the cross-sectional view colored according to the determined cross-sectional color coding EEE 7 is the method of any of EEEs 4-6, wherein receiving the location and/or angle, relative to the target sample, of the target section through the target sample includes: providing, on a display, a visual indication of the volumetric density information; and receiving, from a user interface, an indication of a location and/or an angle of the target section relative to the visual indication of the volumetric density information.

EEE 8 is the method of any of EEEs 4-6, wherein receiving the location and/or angle, relative to the target sample, of the target section through the target sample includes determining, by a controller, the location and/or angle based on the volumetric density information.

EEE 9 is the method of EEE 8, wherein receiving the location and/or angle, relative to the target sample, of the target section through the target sample further includes: providing, on a display, a visual indication of the volumetric density information and of the location and/or angle of the target section relative to the visual indication of the volumetric density information; and receiving, from a user interface, an indication of an update to the determined location and/or an angle of the target section relative to the visual indication of the volumetric density information.

EEE 10 is the method of any of EEEs 8-9, wherein determining, by the controller, the location and/or angle based on the volumetric density information includes: determining, based on the volumetric density information, a segmentation map of one or more volumes of interest within the target sample; and determining the location and/or angle of the target section through the target sample such that the target section passes through a section of the segmentation map having at least one of an increased area or an increased greatest dimension relative to an alternative section of the segmentation map.

EEE 11 is the method of any of EEEs 4-10, further including: causing an actuator to align a sectioning tool with the target sample according to the received location and/or angle of the target section.

EEE 12 is the method of EEE 11, further including: subsequent to causing the actuator to align the sectioning tool with the target sample according to the received location and/or angle of the target section, causing the sectioning tool to section the target sample.

EEE 13 is the method of any of EEEs 4-10, further including: detecting a location and/or an angle of a sectioning tool relative to the target sample; and providing, on a display, an indication of the detected location and/or angle of the sectioning tool relative to the received location and/or angle of the target section.

EEE 14 is the method of any of EEEs 4-13, wherein receiving the location and/or angle, relative to the target sample, of the target section through the target sample includes receiving both of a location and an angle of the target section relative to the target sample.

EEE 15 is the method of any preceding EEE, wherein receiving volumetric density information about the target sample includes causing a micro-CT imager to generate the volumetric density information, wherein the micro-CT imager includes an X-ray source, an X-ray imager, and a sample receptacle configured to contain the target sample, wherein the X-ray source and the X-ray imager define a field of view, and wherein causing the micro-CT imager to generate the volumetric density information includes rotating the sample receptacle and causing the X-ray source and the X-ray imager to generate a plurality of X-ray images of the target sample.

EEE 16 is the method of EEE 15, wherein providing the indication of the location of the at least one region of interest within the target sample includes providing the indication of the location of the at least one region of interest within the target sample while the target sample is located within the micro-CT imager.

EEE 17 is the method of EEE 15, wherein the sample receptacle is removable from the micro-CT imager, wherein the sample receptacle includes a fiducial, and wherein the method further includes: determining, based on the volumetric density information, a location of the fiducial within the volumetric density information.

EEE 18 is the method of any of EEEs 1-17, wherein providing an indication of the location of the at least one region of interest within the target sample comprises: (i) receiving, by a user interface of a terminal device, a user input; (ii) transmitting, by a communications interface of the terminal device to a remote device, an indication of updated image data that is related to the user input; (iii) generating, by one or more processors of the remote device in response to receiving the indication transmitted by the communications interface of the terminal device and based on the volumetric density information, an updated image that is indicative of the location of the at least one region of interest within the target sample; and (iv) transmitting, by the remote device to the communications interface of the terminal device, an indication of the updated image.

EEE 19 is a method including: (i) receiving volumetric density information about a target sample; (ii) detecting a location and/or an angle of a sectioning tool relative to the target sample; and (iii) providing, on a display, a visual indication of the volumetric density information and an indication of the detected location and/or angle of the sectioning tool relative to the volumetric density information.

EEE 20 is the method of EEE 19, further including: determining, based on the volumetric density information, a location of at least one region of interest within the target sample, wherein providing the visual indication of the volumetric density information includes providing an indication of the location of the at least one region of interest within the target sample.

EEE 21 is the method of EEE 20, wherein determining the location of at least one region of interest within the target sample includes determining, based on the volumetric density information, a location of at least one of: a staple, a tumor, a wire, an accumulation of a contrast agent, a duct, a blood vessel, or a calcification.

EEE 22 is the method of any of EEEs 20-21, wherein determining the location of at least one region of interest within the target sample includes: determining, based on the volumetric density information, an outer surface of the target sample; determining, based on the volumetric density information, a segmentation map of one or more volumes of interest within the target sample; and based on the determined outer surface of the target sample and the determined segmentation map, determining a segmentation surface color coding for the segmentation map that color-codes a plurality of points on a surface of the segmentation map according to their respective distances to respective nearest points on the determined outer surface of the target sample, wherein providing the indication of the location of the at least one region of interest within the target sample includes providing an indication of location the segmentation map within the target sample and with the segmentation map colored according to the determined segmentation surface color coding.

EEE 23 is the method of any of EEEs 19-22, further including: receiving a location and/or an angle, relative to the target sample, of a target section through the target sample, wherein providing the indication of the location of the at least one region of interest within the target sample includes providing an indication of the received location and/or angle of the target section within the target sample.

EEE 24 is the method of EEE 23, further including: providing, on the display, a two-dimensional visual depiction of the volumetric density information along the target section through the target sample.

EEE 25 is the method of EEE 24, further including: based on the volumetric density information, determining a cross-sectional color coding for the target section that color-codes a plurality of points across the target section based on the density of respective proximate portions of the volumetric density information, wherein providing, on the display, the two-dimensional visual depiction of the volumetric density information along the target section through the target sample includes providing, on the display, a cross-sectional view of the of the target sample along the target section with the cross-sectional view colored according to the determined cross-sectional color coding EEE 26 is the method of any of EEEs 23-25, wherein receiving the location and/or angle, relative to the target sample, of the target section through the target sample includes: receiving, from a user interface, an indication of a location and/or an angle of the target section relative to the visual indication of the volumetric density information.

EEE 27 is the method of any of EEEs 23-25, wherein receiving the location and/or angle, relative to the target sample, of the target section through the target sample includes determining, by a controller, the location and/or angle based on the volumetric density information.

EEE 28 is the method of EEE 27, wherein receiving the location and/or angle, relative to the target sample, of the target section through the target sample further includes: providing, on the display, a visual indication of the volumetric density information and of the location and/or angle of the target section relative to the visual indication of the volumetric density information; and receiving, from a user interface, an indication of an update to the location and/or angle of the target section relative to the visual indication of the volumetric density information.

EEE 29 is the method of any of EEEs 27-28, wherein determining, by the controller, the location and/or angle based on the volumetric density information includes: determining, based on the volumetric density information, a segmentation map of one or more volumes of interest within the target sample; and determining the location and/or angle of the target section through the target sample such that the target section passes through a section of the segmentation map having at least one of an increased area or an increased greatest dimension relative to an alternative section of the segmentation map.

EEE 30 is the method of any of EEEs 19-29, wherein detecting the location and/or angle, relative to the target sample, of the sectioning tool includes detecting both of a location and an angle of the sectioning tool relative to the target sample.

EEE 31 is the method of any of EEEs 19-29, wherein receiving volumetric density information about the target sample includes causing a micro-CT imager to generate the volumetric density information, wherein the micro-CT imager includes an X-ray source, an X-ray imager, and a sample receptacle configured to contain the target sample, wherein the X-ray source and the X-ray imager define a field of view, and wherein causing the micro-CT imager to generate the volumetric density information includes rotating the sample receptacle and causing the X-ray source and the X-ray imager to generate a plurality of X-ray images of the target sample.

EEE 32 is the method of EEE 31, wherein detecting the location and/or angle of the sectioning tool relative to the target sample includes detecting the location and/or angle of the sectioning tool relative to the target sample while the target sample is located within the micro-CT imager.

EEE 33 is the method of EEE 31 wherein the sample receptacle is removable from the micro-CT imager, wherein the sample receptacle includes a fiducial, and wherein the method further includes: determining, based on the volumetric density information, a location of the fiducial within the volumetric density information.

EEE 34 is a method including: (i) receiving volumetric density information about a target sample; (ii) receiving a location and/or an angle, relative to the volumetric density information, of a target section through the target sample; and (iii) causing an actuator to align a sectioning tool with the target sample according to the received location and/or angle of the target section.

EEE 35 is the method of EEE 34, further including: providing, on a display, a visual indication of the volumetric density information and an indication of the received location and/or angle of the target section relative to the volumetric density information.

EEE 36 is the method of EEE 35, further including: determining, based on the volumetric density information, a location of at least one region of interest within the target sample, wherein providing the visual indication of the volumetric density information includes providing an indication of the location of the at least one region of interest within the target sample.

EEE 37 is the method of EEE 36, wherein determining the location of at least one region of interest within the target sample includes determining, based on the volumetric density information, a location of at least one of: a staple, a tumor, a wire, an accumulation of a contrast agent, a duct, a blood vessel, or a calcification.

EEE 38 is the method of any of EEEs 36-37, wherein determining the location of at least one region of interest within the target sample includes: determining, based on the volumetric density information, an outer surface of the target sample; determining, based on the volumetric density information, a segmentation map of one or more volumes of interest within the target sample; and based on the determined outer surface of the target sample and the determined segmentation map, determining a segmentation surface color coding for the segmentation map that color-codes a plurality of points on a surface of the segmentation map according to their respective distances to respective nearest points on the determined outer surface of the target sample, wherein providing the indication of the location of the at least one region of interest within the target sample includes providing an indication of location the segmentation map within the target sample and with the segmentation map colored according to the determined segmentation surface color coding.

EEE 39 is the method of any of EEEs 35-38, further including: providing, on the display, a two-dimensional visual depiction of the volumetric density information along the target section through the target sample.

EEE 40 is the method of EEE 39, further including: based on the volumetric density information, determining a cross-sectional color coding for the target section that color-codes a plurality of points across the target section based on the density of respective proximate portions of the volumetric density information, wherein providing, on the display, the two-dimensional visual depiction of the volumetric density information along the target section through the target sample includes providing, on the display, a cross-sectional view of the of the target sample along the target section with the cross-sectional view colored according to the determined cross-sectional color coding EEE 41 is the method of any of EEEs 35-40, wherein receiving the location and/or angle, relative to the volumetric density information, of the target section through the target sample includes: receiving, from a user interface, an indication of a location and/or an angle of the target section relative to the visual indication of the volumetric density information.

EEE 42 is the method of any of EEEs 35-40, wherein receiving the location and/or angle, relative to the volumetric density information, of the target section through the target sample includes: determining, by a controller, the location and/or angle based on the volumetric density information; and receiving, from a user interface, an indication of an update to the determined location and/or an angle of the target section relative to the visual indication of the volumetric density information.

EEE 43 is the method of any of EEEs 34-42, further including: subsequent to causing the actuator to align the sectioning tool with the target sample according to the received location and/or angle of the target section, causing the sectioning tool to section the target sample.

EEE 44 is the method of EEE 43, further including: receiving, from a user interface, a command to section the target sample, wherein causing the sectioning tool to section the target sample is performed responsive to receiving the command to section the target sample.

EEE 45 is the method of any of EEEs 34-44, wherein receiving the location and/or angle, relative to the target sample, of the target section through the target sample includes determining, by a controller, the location and/or angle based on the volumetric density information.

EEE 46 is the method of EEE 45, wherein determining, by the controller, the location and/or angle based on the volumetric density information includes: determining, based on the volumetric density information, a segmentation map of one or more volumes of interest within the target sample; and determining the location and/or angle of the target section through the target sample such that the target section passes through a section of the segmentation map having at least one of an increased area or an increased greatest dimension relative to an alternative section of the segmentation map.

EEE 47 is the method of any of EEEs 34-46, wherein receiving the location and/or angle, relative to the volumetric density information, of the target section includes receiving both of a location and an angle of the target section relative to the volumetric density information.

EEE 48 is the method of any of EEEs 34-47, wherein receiving volumetric density information about the target sample includes causing a micro-CT imager to generate the volumetric density information, wherein the micro-CT imager includes an X-ray source, an X-ray imager, and a sample receptacle configured to contain the target sample, wherein the X-ray source and the X-ray imager define a field of view, and wherein causing the micro-CT imager to generate the volumetric density information includes rotating the sample receptacle and causing the X-ray source and the X-ray imager to generate a plurality of X-ray images of the target sample.

EEE 49 is the method of EEE 48, wherein causing the actuator to align the sectioning tool with the target sample includes causing the actuator to align the sectioning tool with the target sample while the target sample is located within the micro-CT imager.

EEE 50 is the method of EEE 48 wherein the sample receptacle is removable from the micro-CT imager, wherein the sample receptacle includes a fiducial, and wherein the method further includes: determining, based on the volumetric density information, a location of the fiducial within the volumetric density information.

EEE 51 is a non-transitory computer-readable medium, configured to store at least computer-readable instructions that, when executed by one or more processors of a computing device, causes the computing device to perform controller operations to perform the method of any of EEEs 1-50.

EEE 52 is a system including: (i) a controller including one or more processors; and (ii) a non-transitory readable medium having stored therein computer-readable instructions that, when executed by the one or more processors of the controller, cause the system to perform the method of any of EEEs 1-50.

We claim:

1. A computer-readable medium, configured to store at least computer-readable instructions that, when executed by one or more processors of a computing device, causes the computing device to perform controller operations comprising:
   receiving volumetric density information about a target sample;
   determining, based on the volumetric density information, a location of at least one region of interest within the target sample; and
   providing an indication of the location of the at least one region of interest within the target sample, wherein providing the indication comprises at least one of: (i) projecting, onto the target sample, a visual pattern that is indicative of the location of the at least one region of interest within the target sample, or (ii) providing, via a display of a head-mounted display, a visual pattern such that the location of the at least one region of interest within the target sample is, from a perspective of a wearer of the head-mounted display, indicated across a surface of the target sample.

2. The computer-readable medium of claim 1, wherein determining the location of at least one region of interest within the target sample comprises determining, based on the volumetric density information, a location of at least one of: a staple, a tumor, a wire, an accumulation of a contrast agent, a duct, a blood vessel, or a calcification.

3. The computer-readable medium of claim 1, wherein determining the location of at least one region of interest within the target sample comprises:
   determining, based on the volumetric density information, an outer surface of the target sample;
   determining, based on the volumetric density information, a segmentation map of one or more volumes of interest within the target sample; and
   based on the determined outer surface of the target sample and the determined segmentation map, determining a segmentation surface color coding for the segmentation map that color-codes a plurality of points on a surface of the segmentation map according to their respective distances to respective nearest points on the determined outer surface of the target sample,
   wherein providing the indication of the location of the at least one region of interest within the target sample comprises providing an indication of location the segmentation map within the target sample and with the segmentation map colored according to the determined segmentation surface color coding.

4. The computer-readable medium of claim 1, wherein the controller operations further comprise:
   receiving a location and/or an angle, relative to the target sample, of a target section through the target sample, wherein providing the indication of the location of the at least one region of interest within the target sample comprises providing an indication of the received location and/or angle of the target section within the target sample.

5. The computer-readable medium of claim 4, wherein the controller operations further comprise:
   providing, on a display, a two-dimensional visual depiction of the volumetric density information along the target section through the target sample.

6. The computer-readable medium of claim 5, wherein the controller operations further comprise:
   based on the volumetric density information, determining a cross-sectional color coding for the target section that color-codes a plurality of points across the target section based on the density of respective proximate portions of the volumetric density information, wherein providing, on the display, the two-dimensional visual depiction of the volumetric density information along the target section through the target sample comprises providing, on the display, a cross-sectional view of the of the target sample along the target section with the cross-sectional view colored according to the determined cross-sectional color coding.

7. The computer-readable medium of claim 4, wherein receiving the location and/or angle, relative to the target sample, of the target section through the target sample comprises:
   providing, on a display, a visual indication of the volumetric density information; and
   receiving, from a user interface, an indication of a location and/or an angle of the target section relative to the visual indication of the volumetric density information.

8. The computer-readable medium of claim 4, wherein receiving the location and/or angle, relative to the target sample, of the target section through the target sample comprises determining the location and/or angle based on the volumetric density information.

9. The computer-readable medium of claim 8, wherein receiving the location and/or angle, relative to the target sample, of the target section through the target sample further comprises:
   providing, on a display, a visual indication of the volumetric density information and of the location and/or angle of the target section relative to the visual indication of the volumetric density information; and
   receiving, from a user interface, an indication of an update to the determined location and/or an angle of the target section relative to the visual indication of the volumetric density information.

10. The computer-readable medium of claim 8, wherein determining the location and/or angle based on the volumetric density information comprises:
    determining, based on the volumetric density information, a segmentation map of one or more volumes of interest within the target sample; and
    determining the location and/or angle of the target section through the target sample such that the target section passes through a section of the segmentation map having at least one of an increased area or an increased greatest dimension relative to an alternative section of the segmentation map.

11. The computer-readable medium of claim 4, wherein the controller operations further comprise:
causing an actuator to align a sectioning tool with the target sample according to the received location and/or angle of the target section.

12. The computer-readable medium of claim 11, wherein the controller operations further comprise:
subsequent to causing the actuator to align the sectioning tool with the target sample according to the received location and/or angle of the target section, causing the sectioning tool to section the target sample.

13. The computer-readable medium of claim 4, wherein the controller operations further comprise:
detecting a location and/or an angle of a sectioning tool relative to the target sample; and
providing, on a display, an indication of the detected location and/or angle of the sectioning tool relative to the received location and/or angle of the target section.

14. The computer-readable medium of claim 4, wherein receiving the location and/or angle, relative to the target sample, of the target section through the target sample comprises receiving both of a location and an angle of the target section relative to the target sample.

15. The computer-readable medium of claim 1, wherein receiving volumetric density information about the target sample comprises causing a micro-CT imager to generate the volumetric density information, wherein the micro-CT imager comprises an X-ray source, an X-ray imager, and a sample receptacle configured to contain the target sample, wherein the X-ray source and the X-ray imager define a field of view, and wherein causing the micro-CT imager to generate the volumetric density information comprises rotating the sample receptacle and causing the X-ray source and the X-ray imager to generate a plurality of X-ray images of the target sample.

16. The computer-readable medium of claim 15, wherein providing the indication of the location of the at least one region of interest within the target sample comprises providing the indication of the location of the at least one region of interest within the target sample while the target sample is located within the micro-CT imager.

17. The computer-readable medium of claim 15, wherein the sample receptacle is removable from the micro-CT imager, wherein the sample receptacle comprises a fiducial, and wherein the controller operations further comprise:
determining, based on the volumetric density information, a location of the fiducial within the volumetric density information.

18. The computer-readable medium of claim 1, wherein providing an indication of the location of the at least one region of interest within the target sample comprises:
receiving, by a user interface of a terminal device, a user input;
transmitting, by a communications interface of the terminal device to a remote device, an indication of updated image data that is related to the user input;
generating, by one or more processors of the remote device in response to receiving the indication transmitted by the communications interface of the terminal device and based on the volumetric density information, an updated image that is indicative of the location of the at least one region of interest within the target sample; and
transmitting, by the remote device to the communications interface of the terminal device, an indication of the updated image.

19. A computer-readable medium, configured to store at least computer-readable instructions that, when executed by one or more processors of a computing device, causes the computing device to perform controller operations comprising:
receiving volumetric density information about a target sample;
receiving a location and/or an angle, relative to the volumetric density information, of a target section through the target sample; and
causing an actuator to align a sectioning tool with the target sample according to the received location and/or angle of the target section.

20. The computer-readable medium of claim 19, further comprising:
providing, on a display, a visual indication of the volumetric density information and an indication of the received location and/or angle of the target section relative to the volumetric density information.

21. The computer-readable medium of claim 20, further comprising:
determining, based on the volumetric density information, a location of at least one region of interest within the target sample, wherein providing the visual indication of the volumetric density information comprises providing an indication of the location of the at least one region of interest within the target sample.

22. The computer-readable medium of claim 21, wherein determining the location of at least one region of interest within the target sample comprises determining, based on the volumetric density information, a location of at least one of: a staple, a tumor, a wire, an accumulation of a contrast agent, a duct, a blood vessel, or a calcification.

23. The computer-readable medium of claim 21, wherein determining the location of at least one region of interest within the target sample comprises:
determining, based on the volumetric density information, an outer surface of the target sample;
determining, based on the volumetric density information, a segmentation map of one or more volumes of interest within the target sample; and
based on the determined outer surface of the target sample and the determined segmentation map, determining a segmentation surface color coding for the segmentation map that color-codes a plurality of points on a surface of the segmentation map according to their respective distances to respective nearest points on the determined outer surface of the target sample,
wherein providing the indication of the location of the at least one region of interest within the target sample comprises providing an indication of location the segmentation map within the target sample and with the segmentation map colored according to the determined segmentation surface color coding.

24. The computer-readable medium of claim 20, wherein the controller operations further comprise:
providing, on the display, a two-dimensional visual depiction of the volumetric density information along the target section through the target sample.

25. The computer-readable medium of claim 24, wherein the controller operations further comprise:
based on the volumetric density information, determining a cross-sectional color coding for the target section that color-codes a plurality of points across the target section based on the density of respective proximate portions of the volumetric density information, wherein providing, on the display, the two-dimensional visual depiction of the volumetric density information along the target section through the target sample comprises providing, on the display, a cross-sectional view of the of the target sample along the target section with the cross-sectional view colored according to the determined cross-sectional color coding.

26. The computer-readable medium of claim 20, wherein receiving the location and/or angle, relative to the volumetric density information, of the target section through the target sample comprises:
receiving, from a user interface, an indication of a location and/or an angle of the target section relative to the visual indication of the volumetric density information.

27. The computer-readable medium of claim 20, wherein receiving the location and/or angle, relative to the volumetric density information, of the target section through the target sample comprises:
determining the location and/or angle based on the volumetric density information; and
receiving, from a user interface, an indication of an update to the determined location and/or an angle of the target section relative to the visual indication of the volumetric density information.

28. The computer-readable medium of claim 19, wherein the controller operations further comprise:
subsequent to causing the actuator to align the sectioning tool with the target sample according to the received location and/or angle of the target section, causing the sectioning tool to section the target sample.

29. The computer-readable medium of claim 28, wherein the controller operations further comprise:
receiving, from a user interface, a command to section the target sample, wherein causing the sectioning tool to section the target sample is performed responsive to receiving the command to section the target sample.

30. The computer-readable medium of claim 19, wherein receiving the location and/or angle, relative to the target sample, of the target section through the target sample comprises determining the location and/or angle based on the volumetric density information.

31. The computer-readable medium of claim 30, wherein determining the location and/or angle based on the volumetric density information comprises:
determining, based on the volumetric density information, a segmentation map of one or more volumes of interest within the target sample; and
determining the location and/or angle of the target section through the target sample such that the target section passes through a section of the segmentation map having at least one of an increased area or an increased greatest dimension relative to an alternative section of the segmentation map.

32. The computer-readable medium of claim 19, wherein receiving the location and/or angle, relative to the volumetric density information, of the target section comprises receiving both of a location and an angle of the target section relative to the volumetric density information.

33. The computer-readable medium of claim 19, wherein receiving volumetric density information about the target sample comprises causing a micro-CT imager to generate the volumetric density information, wherein the micro-CT imager comprises an X-ray source, an X-ray imager, and a sample receptacle configured to contain the target sample, wherein the X-ray source and the X-ray imager define a field of view, and wherein causing the micro-CT imager to generate the volumetric density information comprises rotating the sample receptacle and causing the X-ray source and the X-ray imager to generate a plurality of X-ray images of the target sample.

34. The computer-readable medium of claim 33, wherein causing the actuator to align the sectioning tool with the target sample comprises causing the actuator to align the sectioning tool with the target sample while the target sample is located within the micro-CT imager.

35. The computer-readable medium of claim 33, wherein the sample receptacle is removable from the micro-CT imager, wherein the sample receptacle comprises a fiducial, and wherein the controller operations further comprise:
determining, based on the volumetric density information, a location of the fiducial within the volumetric density information.

* * * * *